US008569059B2

(12) United States Patent
Hall et al.

(10) Patent No.: US 8,569,059 B2
(45) Date of Patent: Oct. 29, 2013

(54) METHOD OF IDENTIFYING CD4+ CD25+ T-CELLS ACTIVATED TO AN ANTIGEN WHICH EXPRESS CD8

(75) Inventors: Bruce Milne Hall, Strathfield (AU); Suzanne J. Hodgkinson, Strathfield (AU)

(73) Assignee: Newsouth Innovations Pty Limited (AU)

( * ) Notice: Subject to any disclaimer, the term of this patent is extended or adjusted under 35 U.S.C. 154(b) by 880 days.

(21) Appl. No.: 12/376,019

(22) PCT Filed: Aug. 2, 2007

(86) PCT No.: PCT/AU2007/001077
§ 371 (c)(1),
(2), (4) Date: Apr. 30, 2009

(87) PCT Pub. No.: WO2008/014555
PCT Pub. Date: Feb. 7, 2008

(65) Prior Publication Data
US 2011/0311559 A1 Dec. 22, 2011

(30) Foreign Application Priority Data
Aug. 2, 2006 (AU) .................................. 2006904186

(51) Int. Cl.
C12N 5/0783 (2010.01)
(52) U.S. Cl.
USPC ........................................................ 435/377
(58) Field of Classification Search
None
See application file for complete search history.

(56) References Cited

U.S. PATENT DOCUMENTS

| 4,520,110 | A  | 5/1985  | Stryer et al. |
| 4,845,653 | A  | 7/1989  | Conrad et al. |
| 4,876,190 | A  | 10/1989 | Recktenwald |
| 5,342,774 | A  | 8/1994  | Boon et al. |
| 5,622,853 | A  | 4/1997  | Terstappen et al. |
| 5,731,160 | A  | 3/1998  | Melief et al. |
| 6,312,692 | B1 | 11/2001 | Noelle et al. |
| 6,787,154 | B2 | 9/2004  | Albani |
| 6,828,150 | B2 | 12/2004 | Cai et al. |
| 2002/0031787 | A1 | 3/2002 | Maclaren et al. |
| 2003/0049696 | A1 | 3/2003 | Norment et al. |
| 2004/0173778 | A1 | 9/2004 | Roncarolo et al. |
| 2006/0121029 | A1 | 6/2006 | Shiku |

FOREIGN PATENT DOCUMENTS

| CA | 2441213 A1 | 9/2002 |
| DE | 10234200 A1 | 2/2004 |
| EP | 1557172 A1 | 7/2005 |
| EP | 1997884 A1 | 12/2008 |
| JP | 2004-529631 | 9/2004 |
| WO | WO 00/20445 A2 | 4/2000 |
| WO | WO 01/37860 A1 | 5/2001 |
| WO | WO 02/072799 A1 | 9/2002 |
| WO | WO 02/072832 A2 | 9/2002 |
| WO | WO 2004/024174 A1 | 3/2004 |
| WO | WO 2004/067554 A2 | 8/2004 |
| WO | WO 2006/081620 A1 | 8/2006 |
| WO | WO 2007/023491 A2 | 3/2007 |

OTHER PUBLICATIONS

Taams et al., Eur. J. Immunol. 2002. 32: 1621-1630.*
Ildstad et al., Blood. 2005;105:2577-2584.*
Dieckmann et al., J. Exp. Med., vol. 193, No. 11, Jun. 4, 2001 1303-1310.*
Saalmuller et al., Vet Immunol Immunopathol. Sep. 10, 2002;87(3-4):137-45.*
Goldsby et al., Immunology, 5th edition, W.H. Freeman and Company, 2002, pp. 284-285.*
Zuckermann et al., Immunology, 1996, (87) pp. 500-512.*
Heinen et al., Journal of General Virology (2002), 83, 1851-1859.*
Das et al., Proc Natl Acad Sci U S A. Apr. 29, 2003;100(9):5324-9.*
Baecher-Allan et al., Seminars in Immunology 16 (2004) 89-97.*
Avis "Parenteral Preparations", *Remington's Pharmaceutical Sciences 15th Ed.* pp. 1461-1487 (1975).
Deardorff "Isotonic Solutions", *Remington's Pharmaceutical Sciences 15th Ed.* pp. 1405-1412 (1975).
Loken "Immunofluorescence Techniques", *Flow Cytomerty and Sorting 2nd Ed.* pp. 341-353 (1990).
McHugh et al. "The role of suppressor T cells in regulation of immune responses", *Journal of Allergy and Clinical Immunology* 110(5):693-702 (2002).
Papiernik et al. "Natural CD4+ CD25+ regulatory T cells. Their role in the control of superantigen responses", *Immunological Reviews* 182(1)180-189 (2001).
Shapiro "10.1.3 The Identification of Cells in Mixed Populations", *Practical Flow Cytometry 2nd Ed.* pp. 270-274 (1988).
Shapiro "10.2.5 Immunology", *Practical Flow Cytometry 2nd Ed.* pp. 282-283 (1988).
Shevach "CD4+ CD25+ Suppressor T Cells: More Questions Than Answers", *Nature Reviews. Immunology* 2(6):389-400 (2002).
Shevach "Immunofluorescence and Cell Sorting", *Current Protocols in Immunology* pp. 5.0.1-5.0.3 (2002).
U.S. Appl. No. 11/815,420, filed Mar. 27, 2008, Hall et al.
Gately et al. "Regulation of Human Lymphocyte Proliferation by a Heterodimeric Cytokine, IL-12 (Cytotoxic Lymphocyte Maturation Factor)", *J. Immunology* 147(3):874-882 (1991).
Goldsby et al. "Part II Generation of B-Cell and T-Cell Responses", *Immunology 5th Ed.* 236-238 (2002).

(Continued)

*Primary Examiner* — Zachary Skelding
(74) *Attorney, Agent, or Firm* — Myers Bigel Sibley & Sajovec, P.A.

(57) ABSTRACT

The invention relates to a method of identifying CD4+ CD25+ T cells activated to an antigen in a population of T cells, comprising identifying CD4+ CD25+ T cells which express CD8. The invention also relates to a method of isolating CD4+ CD25+ T cells activated to an antigen comprising isolating CD4+ CD25+ T cells which express CD8. The invention also relates to a method of increasing tolerance to an antigen in a subject comprising administering CD4+ CD25+ T cells which express CD8.

11 Claims, 6 Drawing Sheets

(56) References Cited

OTHER PUBLICATIONS

Hall et al. "Studies on naïve CD4+CD25+T cells inhibition of naïve CD4+CD25T cells in mixed lymphocyte cultures", *Transplant Immunology* 18:291-301 (2008).
Perussia et al. "Natural Killer (NK) Cell Stimulatory Factor or IL-12 Has Differential Effects on the Proliferation of TCR-alpha.beta+, TCR-gamma.delta+ T Lymphocytes, and NK Cells", *J. Immunology* 149(11):3495-3502 (1992).
Hoffmann et al. "Large-scale in vitro expansion of polyclonal human CD4+CD25$^{high}$ regulatory T cells", *Blood, Am. Soc. of Hematology* 104(3)895-903 (2004).
Krajina et al. "MHC class II-independent CD25+ CD4+ CD8αβ+ αβ T cells attenuate CD4+ T cell-induced transfer colitis", *Eur. J. Immunology* 34(3):705-714 (2004).
Liotta et al. "Functional features of human CD25+ regulatory thymocytes", *Microbes and Infection* 7:1017-1022 (2005).
Nakamura et al. "IL-2-independent generation of FOXP3+CD4+CD8+CD25+ cytotoxic regulatory T cell lines from human umbilical cord blood", *Experimental Hematology* 35:287-296 (2007).
Suzuki et al. "Suppressive activity mechanisms of novel cytotoxic regulatory T cell lines (HOZOT)", *Cell Biology Research Center, Hayashibara Biochemical Laboratories, Inc.* 36:225 (2006).
Supplementary European Search Report corresponding to European Patent Application No. 07784719.2 dated Jun. 10, 2010.
Grundström et al. "Superantigen-Induced Regulatory T Cells Display Different Suppressive Functions in the Presence or Absence of Natural CD4+ CD25+ Regulatory T Cells In Vivo", *J. Immunology* 170:5008-5017 (2003).
Levings et al. "Human CD25+ CD4+ Regulatory Cells Suppress Naïve and Memory T Cell Proliferation and Can Be Expanded In Vitro without Loss of Function", *J. Exp. Med.* 193(11):1295-1301 (2001).
Mukherjee et al. "CD4+$^{CD25+}$ regulatory T cells generated in response to insulin B:9-23 peptide prevent adoptive transfer of diabetes by diabetogenic T cells", *J. Autoimmunity* 21:221-237 (2003).
Papiernik "Natural CD4+CD25+ regulatory T cells. Their role in the control of superantigen responses", *Immunological Reviews* 182:180-189 (2001).
U.S. Appl. No. 07/517,101, filed May 1, 1990, Leon Terstappen.
Bach "Regulatory T Cells Under Scrutiny", *Nature Reviews Immunology* 3:189-198 (2003).
Bhardwaj "Processing and presentation of antigens by dendritic cells: implications for vaccines", *Trends in Molecular Medicine* 7(9):388-394 (2001).
Chen et al. "CD4+, $^{CD25+}$ T cells as Regulators of Alloimmune Responses", *Transplantation Proc.* 33:163-164 (2001).
Crispin et al. "Immunoregulatory T cells in autoimmunity", *Autoimmunity Reviews* 3:45-51 (2004).
Goodnow "Pathways for self-tolerance and the treatment of autoimmune diseases", *The Lancet* 357:2115-2121 (2001).
Graca et al. "Donor-specific transplantation tolerance: The paradoxical behavior of CD4 + CD25+ T cells" *PNAS* 101(27)10122-10126 (2004).
Grundstrom et al. "Superantigen-Induced Regulatory T Cells Display Different Suppressive Functions in the Presence or Absence of Natural CD4 + CD25+ Regulatory T Cells In Vivo", *The Journal of Immunology* 170:5008-5017 (2003).
Hall et al. "The Cellular Basis of Allograft Rejection In Vivo. I. The Cellular Requirements for First-Set Rejection of Heart Grafts", *J. Exp. Med.* 148:878-889 (1978).
Hall et al. "The Cellular Basis of Allograft Rejection In Vivo. III. Restoration of First Set Rejection of Heart Grafts by T Helper Cells in Irradiated Rats", *Transplantation* 36(6):700-705 (1983).
Hall et al. "Specific Unresponsiveness in Rats with Prolonged Cardiac Allograft Survival After Treatment with Cyclosporine. III. Further Characterization of the CD+ 4 Suppressor Cell", *J. Exp. Med.* 171:141-157 (1990).
Hall et al. "Anti-CD4 Monoclonal Antibody-Induced Tolerance to MHC-Incompatible Cardiac Allografts Maintained by CD4+ Suppressor T Cells That Are Not Dependent Upon IL-4$^1$", *The Journal of Immunology* 161:5147-5156 (1998).
He et al. "Treatment with Interleukin-4 Prolongs Allogeneic Neonatal Heart Graft Survival by Inducing T Helper 2 Responses", *Transplantation* 65(9):1145-1152 (1998).
He et al. "Interleukin 13 Cloning From DA Rats", *Transplantation Proc.* 31:1572-1573 (1999).
He et al. "Cloning and Expression of Interleukin-5 from Rats", *Transplantation Proc.* 31:1574-1576 (1999).
He et al. "IL-5 Prolongs Allograft Survival by Downregulating IL-2 and IFN-γ Cytokines", *Transplantation Proc.* 33:703-704 (2001).
Hodgkinson et al. "Transfer of experimental allergic neuritis by intra neural injection of sensitized lymphocytes", *J. Neurological Sci.* 123:162-172 1994.
Horwitz et al. "The role of the combination of IL-2 and TGF-β or IL-10 in the generation and function of CD4+ CD25+ and CD8+ regulatory T cell subsets", *J. Leukocyte Biology* 74:471-478 (2003).
Jiang et al. "Regulatory T Cells in the Control of Transplantation Tolernace and Autoimmunity", *Am J. Transplantation* 3:516-524 (2003).
Jonuleit et al. "Identification and Functional Characterization of Human CD4+ CD25+ T Cells with Regulatory Properties Isolated from Peripheral Blood", *J. Exp. Med.* 193(11):1285-1294 (2001).
Knuth et al. "Cytolytic T-cell clones against an autologous human melanoma: Specificity study and definition of three antigens by immunoselection", *Proc. Natl. Acad. Sci.* 86:2804-2808 (1989).
Kostakis et al. "Prolongation of Rat Heart Allograft Survival by Cyclosporin A", *IRCS Med. Sci.* 5:280 (1977)
Langer "New Methods of Drug Delivery", *Science* 249:1527-1533 (1990).
Levings et al. "Human CD25+ CD4+ T Regulatory Cells Suppress Naïve and Memory T Cell Proliferation and Can Be Expanded In Vitro without Loss of Function", *J. Exp. Med.* 193(11):1295-1301 (2001).
Malek "The main function of IL-2 is to promote the development of T regulatory cells", *J. Leukocyte Biology* 74:961-965 (2003).
Malek et al. "Tolerance, Not Immunity, Crucially Depends on IL-2", *Nature Reviews Immunology* 4:665-674—(2004).
Maus et al. "HLA tetramer-based artificial antigen-presenting cells for stimulation of CD4+ T cells", *Clinical Immunology* 106:16-22 (2003).
Monfardini et al. "Adoptive protection from experimental myasthenia gravis with T cells from mice treated nasally with acetylcholine receptor epitopes", *J. Neuroimmunology* 123:123-134 (2002).
Mukherjee et al. "CD4+ CD25+ regulatory T cells generated in response to insulin B:9-23 peptide prevent adoptive transfer of diabetes by diabetogenic T cells", *J. Autoimmunity* 21:221-237 (2003).
Nelson "IL-2, Regulatory T Cells, and Tolerance", *J. Immunology* 172:3983-3988 (2004).
Nicolls et al. "Induction of Long-Term Specific Tolerance to Allografts in Rats by Therapy with an Anti-CD3-Like Monoclonal Antibody", *Transplantation* 55(3):459-468 (1993).
Nishimura et al. "Induction of antigen-specific immunologic tolerance by in vivo and in vitro antigen-specific expansion of naturally arising Foxp3+ CD25+ CD4+ regulatory T cells", *International Immunology* 16(8):1189-1201 (2004).
Oelke et al. "Ex vivo induction and expansion of antigen-specific cytotoxic T cells by HLA-Ig-coated artificial antigen-presenting cells", *Nature Medicine* 9(5):619-624 (2003).
Pearce et al. "Specific Unresponsiveness in Rats with Prolonged Cardiac Allograft Survival After Treatment with Cyclosporine V. Dependence of CD4+ Suppressor Cells on the Presence of Alloantigen and Cytokines, Including Interleukin 2", *Transplantation* 55(2):374-380 (1993).
Pearce et al. "Specific Unresponsiveness in Rats with Prolonged Cardiac Allograft Survival After Treatment with Cyclosporine VI. In Vitro Alloreactivity of T Cell Subsets from Rats with Long-Surviving Allografts", *Transplantation* 55(2):380-389 (1993).
Plain et al. "Induction of Tolerance with Nondepleting Anti-CD4 Monoclonal Antibodies is Associated with Down-Regulation of TH2 Cytokines", *Transplantation* 64(11):1559-1567 (1997).

(56) References Cited

OTHER PUBLICATIONS

Plain et al. "Induction of Specific Tolerance to Allografts in Rats by Therapy with Non-Mitogenic, Non-Depleting Anti-CD3 Monoclonal Antibody", *Transplantation* 67(4):605-613 (1999).
Read et al. "CD4+ regulatory T cells", *Current Opinion in Immunology* 13:644-649 (2001).
Reid et al. "The control of T cell responses by dendritic cell subsets", *Current Opinion in Immunology* 12:114-121 (2000).
Sakaguchi et al. "Immunologic self tolerance maintained by T-cell-mediated control of self-reactive T cells: implications for autoimmunity and tumor immunity", *Microbes and Infection* 3:911-918 (2001).
Stephens et al. "Phenotypic characterization of regulatory CD4+ CD25+ T cells in rats", *International Immunology* 16(2):365-375 (2003).
Suri-Payer et al. "Differential Cytokine Requirements for Regulation of Autoimmune Gastritis and Colitis by CD4+ CD25+ T Cells", *J. Autoimmunity* 16:115-123 (2001).
Thompson et al. "Regulatory T cells", *Current Opinion in Pharmacology* 4:408-414 (2004).
Tony et al. "Major Histocompatibility Complex-Restricted, Polyclonal B Cell Responses Resulting from Helper T Cell Recognition of Antiimmunoglobulin Presented by Small B Lymphocytes", *J. Exp. Med.* 161:223-241 (1985)
Van den Eynde et al. "Presence on a Human Melanoma of Multiple Antigens Recognized by Autologous CTL", *Int. J. Cancer* 44:634-640 (1989).
Wekerle "Transplantation Tolerance Induced by Mixed Chimerism", *J. Heart Lung Transplant* 20:816-823 (2001).
Baecher-Allan et al. "Human CD4+CD25+ regulatory T cells", *Seminars in Immunology* 16:89-97 (2004).
Cope "Studies of T-cell activation in chronic inflammation", *Arthritis Res* 4(suppl 3):S197-S211 (2002).
Fawcett et al. "Mapping the Homotypic Binding Sites in CD31 and the Role of CD31 Adhesion in the Formation of Interendothelial Cell Contacts", *The Journal of Cell Biology* 128(6):1229-1241 (1995).
Graber et al. "Identification of Key Charged Residues of Human Interleukin-5 in Receptor Binding and Cellular Activation", *The Journal of Biological Chemistry* 270(26):15762-15769 (1995).
Harber et al. "The role of cytokines in immunological tolerance: potential for therapy", *Expert Rev. Mol. Med.* 2(7):1-20 (2000.
Janeway et al. "The target of T cell-mediated autoimmunity is difficult to identify owing to the nature of T-cell ligands", *Immunobiology*, Garland Press 520-522 (2001).
Kelchtermans et al. "Defective CD4+CD25+ regulatory T cell functioning in collagen-induced arthritis: an important factor in pathogenesis, counter-regulated by endogenous IFN-y" *Arthritis Res Ther* 7(2):R402-R415 (2005).
Motulsky "The link between error bars and statistical significance" 3 pages http://www.graphpad.com/articles/errorbars.htm Nov. 2010.
Plugariu et al. "Multisite Mutagenesis of Interleukin 5 Differentiates Sites for Receptor Recognition and Receptor Activation" *Biochemistry* 39:14939-14949 (2000).
Verma et al, "CD4+CD25+ T cells alloactivated ex vivo by IL-2 or IL-4 become potent alloantigen-specific inhibitors of rejection with different phenotypes, suggesting separate pathways of activation by Th1 and Th2 responses", *Blood* 113(2):479-487 (2009).
Whitty et al. "Small molecule cytokine mimetics", *Chemistry & Biology* 6:R107-R118 (1999).

\* cited by examiner

A. —□— 5 x 10⁶ naive CD4⁺
B. ···—△—··· 5 x 10⁶ naive CD4⁺/0.5 x 10⁶ CD25⁺
C. ········▲········ 5 x 10⁶ naive CD4⁺/0.5 x 10⁶ IL-2 activated CD25⁺
D. ---●--- 5 x 10⁶ naive CD4⁺/0.5 x 10⁶ IL-2 activated CD25⁺ CD8⁻

METHOD OF IDENTIFYING CD4+ CD25+ T-CELLS ACTIVATED TO AN ANTIGEN WHICH EXPRESS CD8

RELATED APPLICATIONS

The present application is a 35 U.S.C. §371 national phase application of PCT International Application No. PCT/AU2007/001077, having an international filing date of Aug. 2, 2007 and claiming priority to Australian Patent Application No. 2006904186, filed Aug. 2, 2006, the disclosures of which are incorporated herein by reference in their entireties. The above PCT International Application was published in the English language and has International Publication No. WO 2008/014555 A1.

FIELD OF THE INVENTION

The invention relates to a method of identifying $CD4^+CD25^+$ T cells activated to an antigen, a method for preparing populations of $CD4^+CD25^+$ T cells activated to an antigen, a method of isolating $CD4^+CD25^+$ T cells activated to an antigen, and the use of cells and populations prepared by such methods for increasing tolerance in a subject.

BACKGROUND OF THE INVENTION

The immune system provides a mechanism to protect the body against foreign entities such as infectious organisms or foreign antigens. Under normal conditions, the immune system is capable of recognising and eliciting an immune response against foreign entities, while largely ignoring host tissue. The ability of the immune system to ignore host tissue is known as immune tolerance. Immune tolerance also refers to a state where the immune system is adapted to ignore antigens such as transplanted foreign tissues, infected tissues and allergens.

Autoimmune disease occurs when the T cells of a host recognise and react to "self" molecules, that is, molecules produced by the cells of the host. This occurs when specific self molecules interact with proteins on the surface of T cells such that the T cells recognise the molecule as foreign and consequently elicit an immune response against the self molecule.

In tissue transplantation, non-self major histocompatibility antigen present on the foreign tissue contacts the surface of T cells, resulting in T-cell activation against the foreign antigen. This activation ultimately results in allograft or xenograft rejection by the immune system.

Immunosuppressive drugs have been used to prevent allograft rejection, and to treat autoimmune diseases. Immunosuppressive drugs such as cyclosporin A, steroids, azathioprine, anti-T-cell antibodies, rapamycin, mycophenolate mofetil, desoxyspergualine and FK506, typically have undesirable side-effects, and typically require that the subject be administered the drugs for life or at least extended periods of time, thereby placing the subject at considerable risk of conditions due to long term effects of the treatment.

It would therefore be advantageous to provide an alternative method of decreasing the immune response to an antigen in a subject.

SUMMARY OF THE INVENTION $CD4^+$ T cells are a subset of lymphocytes and are central to inducing an immune response in a human or animal body. $CD4^+CD25^+$ T cells are a subpopulation of $CD4^+$ T cells which represent approximately 1% to 10% of the total $CD4^+$ T cell population in a human or animal body.

$CD4^+CD25^+$ T cells activated to an antigen are capable of imparting to cells of the immune system, including $CD4^+CD25^-$ T cell populations, tolerance to that antigen, and may induce tolerance to other antigens.

The inventors have previously found that $CD4^+CD25^+$ T cells activated to an antigen are formed when naïve $CD4^+CD25^+$ T cells contact an antigen under condition which support activation of the $CD4^+CD25^+$ T cells (see international application no. PCT/AU2006/000133, publication no. WO 2006/081620).

The inventors have found that only a portion of a population of naïve $CD4^+CD25^+$ T cells that is contacted with an antigen under conditions which support activation of the $CD4^+CD25^+$ T cells is activated to the antigen. The inventors have now found that the portion of the population of $CD4^+CD25^+$ T cells that is activated to an antigen expresses CD8, and accordingly, CD8 expression may be used as a marker to identify $CD4^+CD25^+$ T cells that are activated to an antigen. The inventors have found that by using CD8 as a marker to identify $CD4^+CD25^+$ T cells activated to an antigen, these cells can be concentrated or isolated to provide populations of $CD4^+CD25^+$ T cells having a high proportion of $CD4^+CD25^+$ T cells activated to an antigen. The inventors have found that such populations may be administered to subjects to increase tolerance, and in particular, increase tolerance to the antigen to which the cells are activated.

In a first aspect, the invention provides a method of identifying $CD4^+CD25^+$ T cells activated to an antigen in a population of T cells, comprising identifying $CD4^+CD25^+$ T cells which express CD8.

Typically, the $CD4^+CD25^+$ T cells which express CD8 are $CD4^+CD8^+CD25^+$ T cells.

In one embodiment, the population of T cells includes cells other than $CD4^+CD25^+$ T cells.

In a second aspect, the invention provides a method of preparing a population of $CD4^+CD25^+$ T cells activated to an antigen, comprising:
(a) providing a population of $CD4^+CD25^+$ T cells comprising $CD4^+CD25^+$ T cells activated to an antigen; and
(b) treating the population of $CD4^+CD25^+$ T cells to increase the ratio of $CD4^+CD25^+$ T cells which express CD8 to other $CD4^+CD25^+$ T cells.

The population of $CD4^+CD25^+$ T cells may be a population of T cells depleted of $CD25^-$ T cells. The population of $CD4^+CD25^+$ T cells may be a population of T cells depleted of $CD8^+CD25^-$ T cells. The population of $CD4^+CD25^+$ T cells may be a population of T cells depleted of $CD4^+CD25^-$ and $CD8^+CD25^-$ T cells.

A population of T cells may be depleted of $CD25^-$ T cells using a factor which inhibits or prevents proliferation of $CD25^-$ T cells. Factors which inhibit or prevent proliferation of $CD25^-$ T cells include antibodies or compounds which inhibit or prevent proliferation of $CD25^-$ T cells.

Typically, the $CD4^+CD25^+$ T cells which express CD8 are $CD4^+CD8^+CD25^+$.

In one embodiment, the ratio of $CD4^+CD25^+$ T cells which express CD8 to other $CD4^+CD25^+$ T cells is increased by isolating the $CD4^+CD25^+$ T cells which express CD8 from other $CD4^+CD25^+$ T cells in the population. $CD4^+CD25^+$ T cells which express CD8 may be isolated by selecting $CD4^+CD25^+$ T cells which express CD8 from the population of $CD4^+CD25^+$ T cells. $CD4^+CD25^+$ T cells which express CD8 may be isolated by depleting $CD4^+CD25^+$ T cells that do not express CD8 from the population of $CD4^+CD25^+$ T cells.

The method of the second aspect may comprise the further step, after step (b), of (c) growing the population of CD4+, CD25+ T cells activated to the antigen.

The population of CD4+CD25+ T cells activated to an antigen may be grown by culturing the population of CD4+ CD25+ T cells activated to an antigen in the presence of at least one factor capable of supporting proliferation of CD4+ CD25+ T cells activated to an antigen.

In a third aspect, the invention provides a method of isolating CD4+CD25+ T cells activated to an antigen, comprising:
(a) providing a population of T cells comprising CD4+CD25+ T cells activated to an antigen; and
(b) isolating CD4+CD25+ T cells which express CD8.

The population of T cells may be a population of CD4+ CD25+ T cells depleted of CD25− T cells. The population of T cells may be a population of CD4+CD25+ T cells depleted of CD8+CD25− T cells. The population of T cells may be a population of CD4+CD25+ T cells depleted of CD4+CD25− and CD8+CD25− T cells.

The CD25− T cells may be depleted using a factor which inhibits or prevents proliferation of CD25− T cells. Factors which inhibit or prevent proliferation of CD25− T cells include antibodies or compounds which inhibit or prevent proliferation of CD25− T cells.

Typically, the CD4+CD25+ T cells which express CD8 are CD4+CD8+CD25+.

CD4+CD25+ T cells which express CD8 may be isolated from the population of T cells by selecting CD4+CD25+ T cells which express CD8 from the population of T cells. CD4+CD25+ T cells which express CD8 may be isolated from a population of T cells by isolating CD4+CD25+ T cells and depleting CD4+CD25+ T cells that do not express CD8 from the population of T cells.

In a fourth aspect, the invention provides a method of preparing a population of CD4+CD25+ T cells activated to an antigen comprising isolating CD4+CD25+ T cells activated to an antigen by the method of the third aspect, followed by growing the isolated CD4+CD25+ T cells.

The isolated CD4+CD25+ T cells activated to an antigen may be grown by culturing the CD4+CD25+ T cells in the presence of at least one factor capable of supporting proliferation of CD4+CD25+ T cells activated to an antigen.

In a fifth aspect, the invention provides a population of CD4+CD25+ T cells activated to an antigen prepared by the method of the second or fourth aspect.

In a sixth aspect, the invention provides CD4+CD25+ T cells activated to an antigen, isolated from a population of CD4+CD25+ T cells prepared by the method of the second or fourth aspect.

In a seventh aspect, the invention provides CD4+CD25+ T cells activated to an antigen, isolated by the method of the third aspect.

In an eighth aspect, the invention provides a composition comprising a population of CD4+CD25+ T cells of the fifth aspect, or CD4+CD25+ T cells of the sixth or seventh aspect.

In an ninth aspect, the invention provides a method of increasing tolerance in a subject, comprising administering to the subject a therapeutically effective amount of a population of the fifth aspect, CD4+CD25+ T cells of the sixth or seventh aspect, or a composition of the eighth aspect.

In an tenth aspect, the invention provides a method of treating a condition in a subject resulting from an immune response to an antigen, comprising administering to the subject a therapeutically effective amount of a population of the fifth aspect, CD4+CD25+ T cells of the sixth or seventh aspect, or a composition of the eighth aspect.

In an eleventh aspect, the invention provides a method of treating a condition in a subject resulting from an immune response to a specific antigen, comprising administering to the subject a therapeutically effective amount of a population of the fifth aspect, CD4+CD25+ T cells of the sixth or seventh aspect, or a composition of the eighth aspect, wherein the CD4+CD25+ T cells are activated to the specific antigen.

Typically, the condition is an autoimmune disease, graft versus host disease, or an allergy.

In an twelfth aspect, the invention provides the use of a population of the fifth aspect, or the CD4+CD25+ T cells of the sixth or seventh aspect, in the manufacture of a medicament for increasing tolerance.

In a thirteenth aspect, the invention provides the use of a population of the fifth aspect, or CD4+CD25+ T cells of the sixth or seventh aspect, in the manufacture of a medicament for treating a condition resulting from an immune response to an antigen.

In a fourteenth aspect, the invention provides use of CD8 as a marker for isolating a CD4+CD25+ T cell activated to an antigen.

In a fifteenth aspect, the invention provide use of an anti-CD8 antibody for the isolation of a CD4+CD25+ T cell activated to an antigen.

In a sixteenth aspect, the invention provides anti-CD8 antibody when used to isolate CD4+CD25+ T cells activated to an antigen.

In a seventeenth aspect, the invention provides a population of CD4+CD25+ T cells comprising, as a percentage of the total number of CD4+CD25+ T cells in the population, more than 20% CD4+CD25+ T cells activated to an antigen. In some embodiments, the population comprises more than 30%, 35%, 40%, 50%, 60%, 70%, 80%, 90%, 95%, 98% or 99% CD4+CD25+ T cells activated to an antigen.

In an eighteenth aspect, the invention provides a composition comprising the population of the seventeenth aspect.

In a nineteenth aspect, the invention provides a method of increasing tolerance in a subject, comprising administering the population of the seventeenth aspect, or the composition of the eighteenth aspect.

In a twentieth aspect, the invention provides a method of treating a condition in a subject resulting from an immune response to an antigen, comprising administering to the subject a therapeutically effective amount of the population of the seventeenth aspect, or the composition of the eighteenth aspect.

In a twenty-first aspect, the invention provides a method of treating a condition in a subject resulting from an immune response to a specific antigen, comprising administering to the subject a therapeutically effective amount of the population of the seventeenth aspect, or the composition of the eighteenth aspect.

In a twenty-second aspect, the invention provides use of a population of the seventeenth aspect in the manufacture of a medicament for treating a condition resulting from an immune response to an antigen.

In a twenty-third aspect, the invention provides use of a population of the seventeenth aspect in the manufacture of a medicament for increasing tolerance.

In a twenty-third aspect, the invention provides a population of CD4+CD25+ T cells comprising, as a percentage of the total number of CD4+CD25+ T cells in the population, more than 20% CD4+CD8+CD25+ T cells. In some embodiments, the population comprises more than 30%, 35%, 40%, 50%, 60%, 70%, 80%, 90%, 95%, 98% or 99% CD4+CD8+CD25+ T cells.

In a twenty-fourth aspect, the invention provides a composition comprising the population of the twenty-third aspect.

In a twenty-fifth aspect, the invention provides a method of increasing tolerance in a subject, comprising administering the population of the twenty-third aspect, or the composition of the twenty-fourth aspect.

In a twenty-sixth aspect, the invention provides a method of treating a condition in a subject resulting from an immune response to an antigen, comprising administering to the subject a therapeutically effective amount of the population of the twenty-third aspect, or the composition of the twenty-fourth aspect.

In a twenty-seventh aspect, the invention provides a method of treating a condition in a subject resulting from an immune response to a specific antigen, comprising administering to the subject a therapeutically effective amount of the population of the twenty-third aspect, or the composition of the twenty-fourth aspect.

In a twenty-eighth aspect, the invention provides use of a population of the twenty-third aspect in the manufacture of a medicament for treating a condition resulting from an immune response to an antigen.

In a twenty-ninth aspect, the invention provides use of a population of the twenty-third aspect in the manufacture of a medicament for increasing tolerance.

In a thirtieth aspect, the invention provides a kit for use in the method of the first, second, third or fourth aspect, comprising an anti-CD8 antibody.

In a thirty-first aspect, the invention provides a kit when used for isolating CD4+CD25+ T cells activated to an antigen, comprising an anti-CD8 antibody.

DETAILED DESCRIPTION OF THE INVENTION

Figure 1:
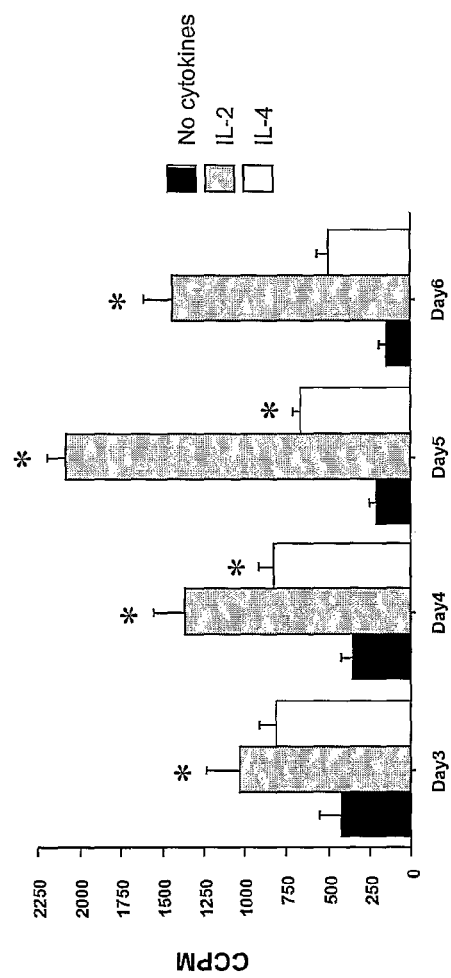
FIG. 1 is a graph showing proliferation (measured as tritium incorporation (CCPM)) from day 3 to day 6 of naïve $CD4^+CD25^+$ T cells cultured with alloantigen and no cytokines (dark shading), cultured with alloantigen and IL-2 (mid-shading) or cultured with alloantigen and IL-4 (light shading).

The invention relates to the use of CD8 expression by $CD4^+$ $CD25^+$ T cells to identify $CD4^+CD25^+$ T cells which are activated to an antigen. $CD4^+CD25^+$ T cells activated to an antigen have suppressor activity and are capable of imparting tolerance to cells of the immune system, including $CD4^+$ $CD25^-$ T cell populations. $CD4^+CD25^+$ T cells activated to an antigen are capable of imparting tolerance to the antigen to which they are activated, and may impart tolerance to other antigens. In other words, $CD4^+CD25^+$ T cells activated to an antigen have suppressor activity. This suppressor activity can be demonstrated by the ability of $CD4^+CD25^+$ T cells activated to an antigen to suppress the proliferation of freshly isolated $CD4^+CD25^-$ T cells in co-culture in response to the antigen, compared to the proliferation of $CD4^+CD25^-$ T cells in response to the antigen in the absence of $CD4^+CD25^+$ T cells activated to the antigen.

The suppressive activity of $CD4^+CD25^+$ T cells activated to an antigen is typically greater than the suppressor activity of naïve $CD4^+CD25^+$ T cells.

In one aspect, the invention provides a method of identifying $CD4^+CD25^+$ T cells activated to an antigen in a population of T cells, comprising identifying $CD4^+CD25^+$ T cells that express CD8.

The population of T cells may be any population of T cells comprising $CD4^+CD25^+$ T cells. The population of T cells may be part of a population of cells comprising cells in addition to T cells. Typically, the population of T cells is a population obtained from a subject, eg. the blood or tissue of a subject.

The subject may be a mammal, such as a mouse, rat, rabbit, horse, camel, pig, cow, sheep, monkey or human. Typically, the subject is a human. For many years, animals of various species such as, for example mice and rats, have been used as models for studying the human immune system as well as the immune system of other mammals. This has been the case because findings in mice and rats, for example, have been directly applicable to models of the immune system of humans and other mammals. Accordingly, results obtained in studies of mice, rats and other mammals are directly applicable to humans and other mammals (Kostakis et al. IRCS Med Sci Libr Compend 1977, 5, 280).

The term "lymphocyte" will be understood by those skilled in the art to refer to the cells of the immune system that are responsible for initiating and controlling the specific immune response. Such cells include T lymphocytes, also known as T cells. CD4$^+$ lymphocytes are T lymphocytes.

The population of T cells may be a mixed lymphocyte population such as mixed peripheral lymphocytes. The population of T cells may be a population of CD4$^+$ T cells isolated from a population containing other lymphocytes, that is, isolated CD4$^+$ T cells. The population of T cells may be isolated CD4$^+$CD25$^+$ T cells.

In some embodiments, the population of T cells is prepared by isolating T cells from a blood or tissue sample from a subject. T cells may be isolated from a blood or tissue sample by methods known in the art, for example, using fluorescence activated cell sorter (FACS), magnetic bead based separation such as magnetic activated cell sorting (MACS) (provided by, for example, Miltenyi Biotec Germany), or the methods described in, for example, U.S. Pat. No. 5,622,853; however, any known procedure for isolating lymphocytes may be used. In one embodiment, the population of T cells is a population of peripheral blood lymphocytes. A population of peripheral blood lymphocytes may be prepared by isolating peripheral blood lymphocytes from a blood sample containing T-cells taken from a subject using methods known in the art such as leukapheresis or the methods for T lymphocyte isolation referred to above. Peripheral blood lymphocytes may also be isolated by Ficoll-Hypaque gradient centrifugation (Pharmacia, Piscataway, N.J.), typically following leukapheresis.

CD4$^+$ T cells may be isolated from a population of T cells, such as isolated peripheral blood lymphocytes, by positive enrichment of CD4$^+$ T cells. CD4$^+$ T cells may be isolated using labeled anti-CD4 monoclonal antibody. Fluorescent or biotin labeled anti-CD4 antibodies and kits for CD4$^+$ T cell isolation or enrichment are available from various commercial sources including Pharmingen/Becton Dickenson, San Diego, Calif.; Miltenyi Biotec, Germany; R&D Systems, USA. Similarly, CD25$^+$ T cells may be isolated from a population of T cells by positive enrichment of CD25$^+$ T cells, for example, isolated using labeled anti-CD25 monoclonal antibody.

In some embodiments, the population of T cells is isolated CD4$^+$CD25$^+$ T cells. CD4$^+$CD25$^+$ T cells may be isolated from a population of T cells, such as isolated peripheral blood lymphocytes, by methods known in the art. As used herein, "CD4$^+$CD25$^+$ T cell" refers to any lymphocyte that expresses on its surface the cluster of differentiation markers known as CD4 and CD25. A CD4$^+$CD25$^+$ T cell is also known as CD4$^+$CD25$^+$ lymphocyte. The CD4$^+$CD25$^+$ T cell may also express other markers which may aid in the isolation of CD4$^+$CD25$^+$ T cells such as, for example, CD45RO$^-$RB$^-$ and Foxp3. Naïve CD4$^+$CD25$^+$ T cells may express L-selectin. Typically, the CD4$^+$CD25$^+$ T cells are CD4$^+$CD25$^{+\ high}$ T cells.

CD4$^+$CD25$^+$ T cells may, for example, be isolated from a population of CD4$^+$ T cells by positive enrichment of CD25$^+$ T cells using an anti-CD25 antibody. CD4$^+$ T cells and CD4$^+$CD25$^+$ T cells may be isolated using panning, affinity separation, cell sorting (eg. using antibodies specific for cell surface markers such as CD4 and/or CD25) and other techniques which provide enrichment of CD4$^+$CD25$^+$ T cells. For example, CD4$^+$CD25$^+$ T cells may be isolated by means of multiparameter flow cytometric analysis using one or more fluorescent labelled anti-CD25 antibodies. This method includes the analysis of both light scatter parameters as well as one or more fluorescence parameters. Other methods of isolation include, for example, magnetic bead based separation as described in, for example, U.S. Pat. No. 517,101. Kits and reagents for magnetic bead based separation such as magnetic activated cell sorting (MACS) kits are commercially available from, for example, Miltenyi Biotec, Germany. Flow cytometric analysis may be performed, for example, on a FACScan™ flow cytometer or a FACStar™ plus cell sorter (both available from Becton Dickinson Immunocytometry Systems, "BDIS"). Data acquisition may be performed with FACScan Research software and FACStar Plus software (BDIS). Forward light scatter, orthogonal light scatter and three fluorescence signals are determined for each cell and stored in listmode data files. The analysis of the listmode data files is preferably performed with Paint-A-Gate, TM software (BDIS). (See U.S. Pat. No. 4,845,653).

The CD4$^+$CD25$^+$ T cells activated to an antigen in the population of T cells may have been activated to the antigen in vivo or ex vivo.

It will be appreciated by those skilled in that art that a population of T cells obtained from a subject may contain CD4$^+$CD25$^+$ T cells activated to an antigen if the subject's CD4$^+$CD25$^+$ T cells have contacted the antigen under conditions which support activation of CD4$^+$CD25$^+$ T cells in vivo.

Accordingly, in some embodiments, a population of T cells, eg. a mixed lymphocyte population, a population of isolated CD4$^+$ T cells or a population of CD4$^+$CD25$^+$ T cells, obtained from a subject will contain CD4$^+$CD25$^+$ T cells activated to an antigen.

In other embodiments, the population of T cells is a population of T cells comprising CD4$^+$CD25$^+$ T cells activated to an antigen, where the CD4$^+$CD25$^+$ T cells were activated to the antigen ex vivo.

In some embodiments, the population of T cells is prepared by obtaining a population of T cells comprising naïve CD4$^+$CD25$^+$ T cells and thereafter activating the CD4$^+$CD25$^+$ T cells ex vivo. The term "naïve CD4$^+$CD25$^+$ T cell" refers to a CD4$^+$CD25$^+$ T cell which has not been contacted by an antigen in the presence of factors which support the activation of CD4$^+$CD25$^+$ T cells. Naïve CD4$^+$CD25$^+$ T cells may be isolated from thymus, bone marrow, peripheral lymphoid tissue or blood. Naïve CD4$^+$CD25$^+$ T cells may be activated ex vivo by contacting naïve CD4$^+$CD25$^+$ T cells with an antigen and culturing the T cells in the presence of one or more factors that support the activation of CD4$^+$CD25$^+$ T cells. Factors which support the activation of CD4$^+$CD25$^+$ T cells include IL-2 and IL-4.

Thus, in one embodiment, CD4$^+$CD25$^+$ T cells may be activated to an antigen ex vivo by contacting naïve CD4$^+$CD25$^+$ T cells with an antigen in the presence of IL-2 and/or IL-4, to thereby activate the CD4$^+$CD25$^+$ T cells. As used herein, a reference to "contacting" a T cell with an antigen, refers to contacting a T cell with an antigen in a manner that permits the T cell to recognise the antigen. Typically, the naïve CD4$^+$CD25$^+$ T cells are contacted with an antigen by presenting the antigen to the T cells on the surface of a stimulator cell such as, for example, an antigen presenting cell. Typically, the antigen is presented to the T cells associated with a major histocompatibility (MHC) molecule on the surface of an antigen presenting cell. As used herein, a "stimulator cell" is a cell which is capable of presenting an antigen to a T cell in a manner in which the T cell can recognise the antigen. For example, the stimulator cell may be a tumour cell (see for example U.S. Pat. No. 5,342,774, Knuth et al. (Proc. Natl. Acad. Sci. USA 86: 2804-2808, 1989) and Van Den Eynde et al. (Int. J. Cancer 44: 634-640, 1989) or the stimulator cell may be an antigen presenting cell.

An "antigen presenting cell" will be understood by those skilled in the art to be a cell which contributes to the induction of an immune response by presenting an antigen to T cells. Antigen presenting cells may be dendritic cells, mononuclear phagocytes, B-lymphocytes, unfractionated lymphocytes or Langerhans cells. The antigen presenting cells may be isolated from, for example, bone marrow, blood, thymus, epidermis, liver or fetal liver. The antigen presenting cells may be unfractionated lymphocytes in which stimulator cells have been impaired by treatment with, for example, irradiation or mitomycin C. The antigen presenting cells may be cells expressing the relevant antigen presenting molecule (eg. Class I or II MHC) and other ligands that are required to facilitate binding and activation of naive $CD4^+CD25^+$ T cells. Such ligands may include ICAM1, ICAM2, LFA3, and the ligands for CD28 and CTL-A and other activation ligands.

The naïve $CD4^+CD25^+$ T cells may be contacted with the antigen using synthetic or artificial antigen presenting systems, such as those described in, for example, U.S. Pat. No. 6,828,150, U.S. Pat. No. 6,787,154, Maus et al. (2003) Clin. Immunol. 106(1): 16-22 or Oelke et al. (2003) Nat. Med. 9(5): 619-624. An example of an artificial antigen presenting system is MHC Class II tetramers in combination with anti-CD28 antibody coated on beads (see, for example, Maus et al. (2003)).

Naïve $CD4^+CD25^+$ T cells may, for example, be activated to an antigen ex vivo by co-culturing the naïve $CD4^+CD25^+$ T cells with antigen presenting cells with the antigen presented on the cell surface at 37° C. in the presence of IL-2 and/or IL-4, for a sufficient length of time to permit proliferation of $CD4^+CD25^+$ T cells activated to the antigen. The resultant population of T cells contains $CD4^+CD25^+$ T cells activated to the antigen.

Typically, the naïve $CD4^+CD25^+$ T cells are co-cultured with the antigen to activate the T cells for not more than 10 days, more typically not more than 8 days, still more typically not more than 5 days, still more typically not more than 4 days, still more typically not more than 3 days.

Without wishing to be bound by theory, the inventors believe that in the case of $CD4^+CD25^+$ T cells that are activated to an antigen in vivo, following contact with the antigen in vivo, activation of the $CD4^+CD25^+$ T cells is supported by the presence of IL-2 and/or IL-4 in vivo.

As used herein, the term "cultured" refers to proliferation or maintenance in a viable state of cells in vitro. The step of culturing $CD4^+CD25^+$ T cells may be accomplished by incubating the T cells in a culture medium which provides sufficient carbon, nitrogen, oxygen and other nutrients, growth factors, buffers, co-factors and any other substance as required to at least maintain the viability of the T cells. For example, T cells may be cultured in RPMI or DMEM supplemented with 10% fetal calf-serum (FCS) and other supplements such as antimicrobial agents, growth factors, other cytokines (see, for example, Transplantation (1993) 55:374-379). Examples of suitable medium include medium formulations that are known to those skilled in the art such as, for example, RPMI, IMDM, DMEM, DMEM/F12, EMEM with or without serum or with reduced serum, and further optionally including antibiotics, lipids, transferrin, insulin, additional nutrient supplements such as amino acids and co-factors as required.

Generally, cultured T cells are incubated at 37° C. in a 5% $CO_2$ atmosphere.

The antigen may be any substance which elicits an immune response in a subject that is not tolerant to the antigen. The antigen may or may not be derived from the subject. The antigen may be an autoantigen, which will be understood by those skilled in the art as referring to an antigen that can elicit a reaction in subjects with a propensity to allergy. The antigen may be an alloantigen, which will be understood by those skilled in the art as referring to an antigen derived from a subject of the same species. The antigen may be a xenoantigen, which will be understood by those skilled in the art as referring to an antigen derived from a subject of a different species. The antigen may be an allergen.

As mentioned above, the antigen may be any substance which elicits an immune response in a subject that is not tolerant to the antigen. For example, when the subject is a human, a typical alloantigen is donor transplant cells or tissue from another human. A typical xenoantigen is transplant cells or tissue from a non-human animal such as, for example, a pig. Donor transplant cells or tissue from humans or non-human animals may include kidney, liver, heart, lung, skin, pancreas, cornea, lens, bone marrow, muscle, connective tissue, vascular tissue, gastrointestinal tissue, nervous tissue, bone, valves, stem cells, or cells, such as stem cells, transfected with an agent such as a therapeutic agent.

An antigen presenting cell may be isolated from a subject with the antigen already presented on the surface of the cell. For example, antigen presenting cells isolated from, for example, the spleen of a subject suffering from an autoimmune disease will have the autoantigen presented on the surface of the cell. In the case of tissue transplantation, antigen presenting cells isolated from the tissue of a transplant donor will have the alloantigen presented on the surface of such cells. For example, the antigen presenting cells may be frozen or stored spleen or lymph node cells from the cadaver of a donor, or peripheral blood cells from a living donor. Alternatively, empty MHC molecules of antigen presenting cells isolated from the subject may be loaded with specific antigens as described in U.S. Pat. No. 5,731,160 whereby empty MHC molecules are loaded with immunogenic exogenous peptides of approximately 8 to 18 amino acids in length.

Antigen presenting cells may be isolated from blood or tissue by methods known in the art. For example, B-lymphocytes can be purified from a mixed population of cells (e.g. other cell types in peripheral blood or spleen) by standard cell separation techniques. For example, adherent cells can be removed by culturing spleen cells on plastic dishes and recovering the non-adherent cell population. T-lymphocytes can be removed from a mixed population of cells treated with an anti-T cell antibody (e.g. anti-CD3 (see for example WO 01/37860), anti-CD2) and complement.

In one embodiment, resting B-lymphocytes are used as the antigen presenting cell. Resting B-lymphocytes can be isolated by methods based on the small size and density of the B-lymphocytes. Resting lymphoid cells may be isolated by counterflow centrifugal elutriation as described in Tony, H-P, Parker, D.C. (1985) J. Exp. Med. 161: 223-241. Using counterflow centrifugal elutriation, a small, resting lymphoid cell population depleted of cells which can activate T cell responses can be obtained as described in U.S. Pat. No. 6,312, 692.

In another embodiment, unfractionated lymphocytes may be used as the antigen presenting cell. Typically, the unfractionated lymphocytes are treated to impair proliferation of stimulator cells. Examples of treatments suitable for impairing proliferation of stimulator cells include irradiation, or treatment with mitomycin C.

In accordance with the present invention, $CD4^+CD25^+$ T cells activated to an antigen are identified in a population of T cells by detecting expression of CD8 by $CD4^+CD25^+$ T cells.

Expression of CD8 may be detected using any method for detecting CD8 gene expression. CD8 gene expression may be detected by detecting expression of mRNA encoding CD8, for example, using RT-PCR, northern hybridization, or other methods known in the art for detecting mRNA expression. Methods of detecting expression of mRNA are described in, for example, Sambrook et al. (1989) Molecular Cloning: A laboratory Manual, Cold Spring Harbor Laboratory Press.

Typically, expression of CD8 by $CD4^+CD25^+$ T cells is detected by detecting expression of CD8 on the surface of $CD4^+CD25^+$ T cells. Such expression may be detected, for example, using anti-CD8 antibody that is labeled. Suitable labels include fluorophores, radiolabels, biotin, alkaline phosphatase, horseradish peroxidase. Suitable fluorophores include phycoerythrin ("PE"), fluorescein isothyocyanate ("FITC") and peridinin chlorophyll complex ("PerCp"), allophycocyanin (APC), Cyanin dye (for example, Cy3, Cy3.5, Cy5, Cy5.5, Cy7). For a description of PE and PerCp, see U.S. Pat. Nos. 4,520,110 and 4,876,190 respectively. Typically, the anti-CD8 antibody is a monoclonal antibody. The monoclonal antibodies which may be used include, for example: anti-CD8 FITC, PE or PerCp. Suitable radiolabels include $I^{125}$, $P^{32}$, $P^{33}$. It is envisaged that fluorescently labeled anti-CD8 antibody may be used in combination with fluorescently labeled anti-CD4 and/or anti-CD25 antibodies to identify $CD4^+CD8^+CD25^+$ T cells. Antibodies fluorescently labeled or labeled with biotin, and kits for the identification and isolation of $CD8^+$ T cells, are commercially available from, for example, R&D Systems, USA; Miltenyi Biotec, Germany; BDIS, USA).

Binding of labelled antibodies to T cells may be detected using methods known in the art, including flow cytometry as described above, affinity separation, panning, magnetic activated sorting (MACS) (reagents and kits for MACS are available from, for example, Miltenyi Biotec, Germany), immunofluorescence, and western blotting. Methods for detecting the binding of labeled antibodies to cells are described in, for example, Antibodies: A Laboratory Manual (Harlow and Lane, Eds) 1988, Cold Spring Harbor Press, Cold Spring Harbor, N.Y.; Immunofluorescence and Cell Sorting. In: Current Protocols in Immunology (J. Coligan, A. Kruisbeck, D. Marguiles, E. Shevach, W, Strober, Eds) John Wiley and Sons, New York; Shapiro (1988) Practical Flow Cytometry, $2^{nd}$ Ed. Wiley-Liss Eds. New York; Loken (1990) Immunofluorescence Tecniques in Flow Cytometry and Sorting, $2^{nd}$ Ed, Wiley. New York.

The ability to identify $CD4^+CD25^+$ T cells activated to an antigen by the method of the present invention, can be used to prepare a population of $CD4^+CD25^+$ T cells which are activated to an antigen. Such populations may be prepared by providing a population of $CD4^+CD25^+$ T cells comprising $CD4^+CD25^+$ T cells activated to the antigen and treating the population of $CD4^+CD25^+$ T cells to increase the ratio of $CD4^+CD25^+$ T cells which express CD8 to other $CD4^+CD25^+$ T cells.

The population of $CD4^+CD25^+$ T cells may be isolated $CD4^+CD25^+$ T cells, or may be part of a larger population of cells. For example, the population of $CD4^+CD25^+$ T cells may be part of a population of $CD4^+$ T cells, part of a population of $CD25^+$ T cells, or part of a mixed lymphocyte population. In some embodiments, the population of $CD4^+CD25^+$ T cells is prepared by treating a population of $CD4^+$ T cells to remove some or all of the $CD25^-$ T cells in the population, that is, a population of $CD4^+CD25^+$ T cells depleted of $CD25^-$ T cells. The population of $CD4^+CD25^+$ T cells may comprise a population of T cells depleted of $CD25^-$ T cells. Typically, the population of $CD4^+CD25^+$ T cells comprises a population of T cells depleted of $CD8^+CD25^-$ T cells. More typically, the population of $CD4^+CD25^+$ T cells comprises a population of $CD4^+CD25^+$ T cells depleted of $CD4^+CD25^-$ and $CD8^+CD25^-$ T cells. Such populations may be prepared using the methods known in the art and described above.

In some embodiments, the proportion of the $CD4^+$ T cells in the population of $CD4^+CD25^+$ T cells which are $CD25^-$ is less than 10%, more typically less than 5%, still more typically less than 2%.

A population of T cells may be depleted of $CD25^-$ T cells using a factor which inhibits or prevents proliferation of $CD25^-$ T cells. Factors which inhibit or prevent proliferation of $CD25^-$ T cells include antibodies (typically monoclonal antibodies) or compounds which inhibit or prevent proliferation of $CD25^-$ T cells. An example of a compound which inhibit or prevent proliferation of $CD25^-$ T cells is rapamycin.

Once the population of $CD4^+CD25^+$ T cells is provided, $CD4^+CD25^+$ T cells which express CD8 in the population of $CD4^+CD25^+$ T cells may be identified using the method of the first aspect of the invention.

Once the population of $CD4^+CD25^+$ T cells is provided, the population of $CD4^+CD25^+$ T cells is treated to provide a population having an increased ratio of $CD4^+CD25^+$ T cells which express CD8 to other $CD4^+CD25^+$ T cells. Typically, the ratio of $CD4^+CD8^+CD25^+$ T cells to $CD4^+CD8^-CD25^+$ T cells is increased.

In some embodiments, the ratio of $CD4^+CD25^+$ T cells which express CD8 to other $CD4^+CD25^+$ T cells is increased to provide a population of $CD4^+CD25^+$ T cells comprising, by number, more than 20% $CD4^+CD25^+$ T cells activated to an antigen. In some embodiments, the resultant population of $CD4^+CD25^+$ T cells comprises more than 30%, 35%, 40%, 50%, 60%, 70%, 80%, 90%, 95%, 98% or 99% $CD4^+CD25^+$ T cells activated to an antigen.

Typically, $CD4^+CD8^+CD25^+$ T cells are isolated from the population of $CD4^+CD25^+$ T cells to thereby increase the ratio of $CD4^+CD25^+$ T cells which express CD8 to other $CD4^+CD25^+$ T cells. $CD4^+CD8^+CD25^+$ T cells may be isolated by selecting $CD8^+$ T cells from the population of $CD4^+CD25^+$ T cells. $CD4^+CD8^+CD25^+$ T cells may be selected from the population of $CD4^+CD25^+$ T cells using anti-CD8 to select those cells that are $CD8^+$, optionally in combination with anti-CD4 and/or anti-CD25 antibodies as described above, in methods such as flow cytometry, panning, MACS, or other affinity separation methods known in the art and described above. Kits for the isolation of $CD8^+$ T cells are commercially available from, for example, Miltenyi Biotec, Germany).

$CD4^+CD25^+$ T cells activated to an antigen isolated by the method of the invention or a population of $CD4^+CD25^+$ T cells activated to an antigen prepared by the method of the invention, may be grown or expanded in vitro by culturing the T cells in the presence of at least one factor capable of supporting proliferation of $CD4^+CD25^+$ T cells activated to an antigen. Examples of factors capable of supporting proliferation of $CD4^+CD25^+$ T cells activated to an antigen include IL-5, IL-12, IL-13, IL-23, TGF-beta, IFN-γ, and nitric oxide inhibitors. Typically, the IL-12 is IL-12p70. The nitric oxide inhibitors may be an inhibitor of nitric oxide synthase. Typically, the nitric oxide synthase inhibitor is an iNOS inhibitor. Examples of suitable iNOS inhibitors include L-NIL (N6-(1-Iminoethyl)-L-lysine), L-NAME (N-nitro-L-arginine-methyl ester), aminoguanidine, GDIPS, FeTPPS, N-(3-aminomethyl)benzyl)acetamidine dihydrochloride.

Thus, the present invention further provides growing the population of $CD4^+CD25^+$ T cells activated to an antigen prepared by the method of the invention, or the $CD4^+CD25^+$ T cells activated to an antigen prepared or isolated by the method of the invention, in vitro by culturing the population of $CD4^+CD25^+$ T cells activated to an antigen prepared by the method of the invention, or the $CD4^+CD25^+$ T cells activated to an antigen prepared or isolated by the method of the invention, in the presence of at least one factor capable of supporting proliferation of $CD4^+CD25^+$ T cells activated to an antigen. The population of $CD4^+CD25^+$ T cells activated to an antigen prepared by the method of the invention, or the $CD4^+CD25^+$ T cells activated to an antigen prepared or isolated by the method of the invention, are typically contacted with an antigen in vitro prior to, or simultaneously with, culturing the population of $CD4^+CD25^+$ T cells activated to, an antigen prepared by the method of the invention, or the $CD4^+CD25^+$ T cells activated to an antigen prepared or isolated by the method of the invention, in the presence of the at least one factor selected from the group consisting of IL-5, IL-12, IL-13, IL-23, TGF-beta, IFN-γ, and a nitric oxide inhibitor. The population of $CD4^+CD25^+$ T cells activated to an antigen prepared by the method of the invention, or the $CD4^+CD25^+$ T cells activated to an antigen prepared or isolated by the method of the invention, may be cultured in the presence of the antigen to which the activated $CD4^+CD25^+$ T cells are activated.

Also provided are populations of $CD4^+CD25^+$ T cells activated to an antigen prepared by the method of the invention, and $CD4^+CD25^+$ T cells activated to an antigen isolated by the method of the invention. Such populations and cells may be included in compositions.

Accordingly, the present invention provides methods which can be used to prepare or isolate a population of $CD4^+CD25^+$ T cells activated to an antigen. The prepared or isolated population may be further grown or expanded in vitro. Accordingly, the present invention provides means for preparing and growing a population of $CD4^+CD25^+$ T cells activated to an antigen. The $CD4^+CD25^+$ T cells activated to an antigen can be used to increase tolerance to an antigen in a subject.

$CD4^+CD25^+$ T cells activated to an antigen isolated, prepared or grown using the methods of the invention, and compositions comprising such cells, may be administered to a subject in need thereof to increase the subject's tolerance to an antigen. Thus, the invention further provides a method for increasing tolerance to an antigen in a subject which comprises administering to the subject a therapeutically effective amount of $CD4^+CD25^+$ T cells activated to an antigen wherein the $CD4^+CD25^+$ T cells activated to an antigen have been isolated, grown or prepared using the methods of the invention.

As used herein, the term "tolerance" refers to the process of suppressing a portion of the immune system that recognises an antigen as being foreign. It will be appreciated by persons skilled in the art that the term "tolerance" as used herein has the same meaning as "immune tolerance".

As used herein, the expression "increasing tolerance" means an increase in tolerance to an antigen relative to the tolerance to the antigen prior to application of the method of the invention.

The $CD4^+CD25^+$ T cells activated to an antigen prepared, isolated or grown by the methods of the present invention are typically used to suppress the immune system of a subject, and are typically used to suppress that portion of the immune system that recognises the antigen to which the $CD4^+CD25^+$ T cells are activated. For example, tolerance may be induced to a specific transplanted tissue, an autoantigen or an allergen.

The $CD4^+CD25^+$ T cells activated to an antigen are typically administered by parenteral administration. Preparations for parenteral administration include suspensions in sterile aqueous carriers. Aqueous carriers for suspensions may include saline and buffered media. Parenteral vehicles include any solution which is capable of maintaining the activity and viability of the lymphocytes, and may include, for example, cell culture medium, sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, anti-microbials, anti-oxidants, chelating agents, growth factors and inert gases and the like.

The $CD4^+CD25^+$ T cells activated to an antigen can be administered, parenterally by injection or by gradual infusion over time independently or together. Administration may be intravenously, intra-arterial, intra-peritoneally, intramuscularly, intra-cavity, intra-articularly, or transdermally. Typically, administration is intravenously.

The administration may be local administration or regional administration to a site of immune activity.

Typically, the $CD4^+CD25^+$ T cells activated to an antigen are administered to obtain a ratio of $CD4^+CD25^+$ T cells activated to the antigen: $CD4^+CD25^-$ T cells in the subject of about 1:1 to about 1:64. Examples of suitable ratios of $CD4^+CD8^+CD25^+$ T cells: $CD4^+CD25^-$ T cells in the subject are: 1:1500, 1:1000, 1:900, 1:500, 1:400, 1:300, 1:200, 1:100, 1:64, 1:56, 1:50, 1:48, 1:42, 1:36, 1:32, 1:28, 1:24, 1:20, 1:16, 1:12, 1:10, 1:8, 1:4, 1:2, 1:1.

In another aspect, the invention provides a method for treating or preventing in a subject in need thereof a condition resulting from an immune response to an antigen. The method comprises administering a therapeutically effective amount of $CD4^+CD25^+$ T cells activated to the antigen which have been isolated, grown or prepared using the methods of the invention, or a composition comprising $CD4^+CD25^+$ T cells activated to the antigen which have been isolated, grown or prepared using the methods of the invention. The disease may be an autoimmune disease, or host-versus-graft disease resulting from allograft or xenograft rejection, or an allergic reaction.

In one embodiment, the disease is an autoimmune disease. As used herein, "autoimmune disease" refers to a disease resulting from an immune response to an autoantigen. Autoimmune diseases include, but are not limited to, the following types of autoimmune diseases: type 1 insulin dependent diabetes mellitis, inflammatory bowel syndrome including ulcerative colitis and Crohn's disease, thrombotic thrombocytopenic purpura, Sjogren's syndrome, encephalitis, acute encephalomyelitis, Guillain Barre Syndrome, chronic inflammatory demyelination polyneuropathy, idiopathic pulmonary fibrosis/alveolitis, asthma, uveitis, iritis, optic neuritis, rheumatic fever, Reiter's syndrome, psoriasis, psoriasis arthritis, multiple sclerosis, progressive systemic sclerosis, primary biliary cirrhosis, pemphigus, pemphigoid, necrotising vasculitis, myasthenia gravis, polymyositis, sarcoidosis, granulomatosis, vasculitis, pernicious anemia, CNS inflammatory disorder, autoimmune haemolytic anaemia, Hashitomo's thyroiditis, Graves disease, habitual spontaneous abortions, Raynaud's syndrome, dermatomyositis, chronic active hepatitis, celiac disease, autoimmune complications of AIDS, atrophic gastritis, ankylosing spondylitis, Addison's disease, atopic dermatitis, allergic rhinitis and conjunctivitis, asthma, chronic demyelinating neuropathy, glomerulonephritis including membranous nephropathy, focal sclerosing glomerulonephritis and minimal change nephropathy, systemic lupus erythematosis, scleroderma, rheumatoid arthritis, and juvenile arthritis.

In another embodiment, the disease is a host-versus-graft disease resulting from allograft rejection. The term "allograft rejection" will be understood by those skilled in the art as referring to an immune response to an antigen(s) of a graft or transplanted tissue in a subject wherein the graft or tissue is obtained from a different member of the same species as the subject.

Allograft rejection includes rejection of all types of allograft and may include for example, allografts of cornea, heart, valves, lung, kidney, liver, pancreas, pancreatic islets, brain, bone, intestine, skin, bone marrow, stem cells, hematopoietic cell or other cells.

In yet another embodiment, the disease is a graft-versus-host disease resulting from bone marrow transplantation or other transplants or lympho-haemopoietic cells such as small bowel transplants.

In another embodiment, the disease is a host versus graft response to a xenograft. The term "xenograft rejection" will be understood by those skilled in the art as referring to an immune response to an antigen(s) of a graft or tissue transplant in a subject wherein the tissue is obtained from a member of a different species from the subject.

Xenograft rejection includes rejection of all types of xenograft and may include for example, xenografts of cornea, heart, lung, kidney, liver, pancreas, pancreatic islets, brain, bone, intestine, skin, valves, bone marrow, stem cells, hematopoietic cells or other cells from, for example, rodent, non-human primate, human, cattle, pig, sheep, camel, goat, kangaroo or horse.

In a further embodiment, the disease is an allergy. The term "allergy" will be understood by those skilled in the art to refer to a type I hypersensitivity that is associated with a T cell response, typically a Th2 response, following contact with an allergen. The allergy may be an allergy to any allergen and includes, for example, asthma, eczema, atopic dermatitis, anaphylaxis, hayfever, allergic conjunctivitis, contact dermatitis, food allergy, drug or any other chemical allergy, fungal allergy, or an allergy as defined above to any other allergens or parts thereof.

Generally, the terms "treat", "treating", "treatment" and the like are used herein to mean affecting a subject to obtain a desired effect. The desired effect may be a biological, pharmacologic and/or physiologic effect. The effect may be prophylactic in terms of completely or partially preventing a disease or sign or symptom of disease, and/or may be therapeutic in terms of completely or partially curing a disease.

The disease may be treated by administering to the subject a therapeutically effective amount of a composition comprising $CD4^+CD25^+$ T cells activated to the antigen which have been isolated, grown or prepared using the methods of the invention and a pharmaceutically acceptable carrier. The composition comprising $CD4^+CD25^+$ T cells activated to the antigen which have been isolated, grown or prepared using the methods of the invention, may be administered parenterally in formulations containing conventional non-toxic pharmaceutically acceptable carriers.

As used herein, the term "therapeutically effective amount" refers to an amount effective to yield a desired therapeutic response. For example, an amount sufficient to prevent or treat autoimmune disease such as those mentioned above.

The specific therapeutically effective amount will vary with such factors as the particular condition being treated, the physical condition of the subject, the type of mammal being treated, the duration of the treatment, the nature of concurrent therapy (if any), and the specific formulations employed and the relative constituent cell populations of the subject's immune system.

As used herein, a "pharmaceutically acceptable carrier" is a pharmaceutically acceptable suspending agent, medium or vehicle for delivering a therapeutic composition to a subject. Pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412, 1461-1487 (1975) and The National Formulary XIV., 14th ed. Washington: American Pharmaceutical Association (1975). The pH and exact concentration of the various components of the composition are adjusted to maintain cell viability and activity according to routine skills in the art. See Goodman and Gilman's The Pharmacological Basis for Therapeutics (7th ed.).

Compositions can be administered, for in vivo application, parentally by injection or by gradual perfusion over time independently or together. Administration may be intravenously, intra-arterial, intra-peritoneally, intramuscularly, intra-cavity, intra-articular, transdermally or subcutaneously.

The compositions are preferably prepared and administered in dose units. For treatment of a subject, depending on the manner of administration, nature and severity of the disorder, age and body weight of the subject, different daily doses can be used. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The compositions according to the invention may be administered systemically, locally or regionally to a site of immune activity, in a therapeutically effective dose. Amounts effective for this use will depend on the severity of the side effects and the weight and general state of the subject. Typically, dosages used in vitro may provide useful guidance in the amounts useful for administration of the composition, and animal models may be used to determine effective dosages. Various considerations are described, eg., in Langer, Science, 249: 1527, (1990).

The compositions may be in the form of a sterile injectable suspension. This suspension may be formulated according to known methods using those agents suitable for suspending and administering cell suspensions which have been mentioned above. Among the acceptable vehicles and solvents that may be employed to suspend cells are cell culture medium, Ringer's solution, and isotonic sodium chloride solution.

Dosage levels of the composition of the present invention may be in the order of about $5 \times 10^4$ to about $5 \times 10^9$ cells per kilogram body weight, with a typical dosage range between about $5 \times 10^6$ to about $5 \times 10^8$ cells per kilogram body weight per day (from about $3 \times 10^8$ cells to about $3 \times 10^{11}$ cells per patient per day). The amount of cells that may be combined with the carrier materials to produce a single dosage will vary depending upon the host treated and the particular mode of administration. For example, a composition intended for administration to humans may contain about $5 \times 10^8$ to $5 \times 10^{10}$ cells with an appropriate and convenient amount of carrier material which may vary from about 5 to 95 percent of the total composition. Dosage unit forms will generally contain between from about 5×10⁸ to 10⁹ cells.

It will be understood, however, that the specific dose level for any particular patient will depend upon a variety of factors including the activity of the cells, the age, body weight, general health, sex, diet, time of administration, drug combination and the severity of the particular disease undergoing therapy.

Also contemplated for use with the methods of the invention are kits. As used herein, the term "kit" refers to a group of components that are capable of being used together in the methods of the invention. For example, the kit may be used to identify $CD4^+CD25^+$ T cells activated to an antigen, to prepare populations of $CD4^+CD25^+$ T cells activated to an antigen, to isolate $CD4^+CD25^+$ T cells activated to an antigen, and may in addition be used to grow $CD4^+CD25^+$ T cells or the populations of $CD4^+CD25^+$ T cells activated to an antigen. A kit may include an anti-CD8 antibody, typically an anti-CD8 monoclonal antibody. The antibody is typically labeled with, for example, a fluorophore (such as those mentioned above), or other detectable label. The kit may in addition comprise anti-CD4 and/or anti-CD25 antibodies. The kit may comprise one or more cytokines selected from the group consisting of IL-2, IL-4, IL-5, IL-12, IL-13, IL-23, TGF-beta and IFN-γ, or a biologically active fragment thereof, isolated protein or a medium such as, for example, a medium suitable for the culturing of lymphocytes. The kit may further comprise antigen and or antigen presenting cells. The kit may further include instructions for applying the method of the invention using the components of the kit.

The invention will now be further described by way of reference only to the following non-limiting examples. It should be understood, however, that the examples following are illustrative only, and should not be taken in any way as a restriction on the generality of the invention described above.

EXAMPLES

A. Animals and Procedures

DA ($RT1^a$), PVG ($RT1^c$) and Lewis ($RT1^l$) rats were bred and maintained as described in J. Immunol. 1998, 161; 5146. Samples of lymph node and spleen cells were prepared as described in J. Exp. Med. 1978, 148; 878.

B. Preparation of Naïve $CD4^+CD25^+$ T Cell Populations

Single cell suspensions from spleen and lymph node cells (LNC) were prepared from DA rats, as described in J. Exp. Med. 1978, 148; 878 and RBC lysed by a buffer of 0.83% $NH_4Cl$, 0.1% $KHCO_3$ and 10 mM EDTA at pH 7.2. Cells were resuspended in PBS/2% BSA (MultiGel, Biosciences, Castle Hill, NSW, Australia).

$CD4^+CD25^+$ T cells subsets were identified by mAb and indirect immunofluorescence staining, and analysis on a FACScan, as described (J. Exp. Med. (1990) 171(1): 141-157). Monoclonal antibodies used were R7.2 (TCR-α,β), G4.18 (CD3), W3/25 or MRCOx35 (CD4), MRCOx8 (CD8), MRCOx39 (CD25, IL-2R alpha chain), L316 (CD122 IL-2R beta chain), (Pharmingen/Becton Dickenson, San Diego, Calif.).

Subsets of naïve $CD4^+CD25^+$ T cells were enriched from mixed lymphocyte culture from DA rats by a combination of an indirect panning technique to deplete $CD8^+$ T cells and B cells (Hall et al. (1983) Transplantation 36: 700), and Magnetic bead separation techniques and a MACS column, as described by the manufacturer, (Miltenyi Biotec, Bergisch Gadenbach, Germany). These cells were incubated for 30 min at 4° C. on Petri dishes (Greiner Labortechnik, Frickenhausen, Germany) coated with rabbit anti-rat Ig and anti-mouse Ig (DAKO A/s. Glostrup, Denmark). This supernatant was concentrated in 85 µl of PBS and incubated at 4° C. for 15 minutes with 13 µl of goat anti-mouse Ig micro-beads (Miltenyi) per $10^6$ cells. After washing, cells were eluted on a CS MACS column (Milentyi) to obtain 97-99% enrichment for $CD4^+$ T cells. The enriched $CD4^+$ T cells were then incubated at 4° C. for 20 min with PE conjugated MRCOx39 (anti-CD25 monoclonal antibody), then washed twice before incubation for 15 min at 4° C. with 8 µl/$10^6$ cells of mouse anti-PE mAb microbeads (Miltenyi). Cells were then eluted through a LS MACS column (Miltenyi) and were resuspended in media with 20% Lewis rat serum for use in MLC. The cells were 96-99% $CD4^+$ and the depleted population had <1% $CD4^+$, $CD25^{+high}$ T cells. The enriched population was 85-95% $CD4^+CD25^{+\ high}$ T cells. For those experienced in the art, it is known that enriched $CD4^+CD25^+$ T cells populations refers to the $CD4^+CD25^{+\ high}$ T cells, as separation techniques preferentially enrich this population of $CD4^+CD25^+$ T cells.

$CD4^+CD25^+$ T cells were also directly enriched by incubation of unfractionated lymphoid cells at 4° C. for 20 min with PE conjugated MRCOx39, then washed twice before incubation for 15 min at 4° C. with mouse anti-PE mAb microbeads (Miltenyi). Cells were then eluted through a LS MACS column (Miltenyi) and were either resuspended in media with 20% Lewis rat serum for use in MLC or in PBS/2% BSA for injection to rats. $CD4^+CD8^+CD25^+$ T cells were isolated by further enriching the $CD4^+CD25^+$ T cells populations for $CD8^+$ expressing cells using anti-CD8 mAB as described above.

C. Mixed Lymphocyte Culture

Stimulator cells were obtained from thymus of either PVG rats (donor) or Lewis rats (third party) rats given 8.5 gray whole body irradiation 24 hours before. This population of stimulator cells is depleted of mature lymphocytes and is enriched for antigen presenting cells. Enriched antigen presenting cells are preferred as functional lymphoid cells will be stimulated and may produce cytokines that will activate responder cells or may produce background stimulation. Stimulator cells from whole body irradiated donors have the peripheral and thymic lymphoid cells destroyed in vivo within 24 hours. An alternate method that could be used to enrich dendritic cells could be with monoclonal antibody selection and Magnetic bead separation. The stimulator cells can also be irradiated and left over night to allow peripheral lymphocytes to die of the effects of irradiation, leaving an antigen presenting cell enriched population. $10^4$ of these stimulator cells were as effective as $2 \times 10^5$ in vitro irradiated spleen cells. The normal ratio of responder to stimulator cells is 1:1 to 2:1 when peripheral lymphoid cells are used as stimulators but when there is enrichment of antigen presenting cells by depletion of T and B lymphocytes then responders to stimulators cells may be 10-100:1.

Microcultures in U-bottom microtiter plates (Linbro, Flow Labs, Va.) had $1 \times 10^4$ stimulators cells and either $1 \times 10^5$ responder cells/well in a total volume of 200 µl. 4-6 replicate wells were set up for each experimental sample. Bulk cultures were grown in 25 cm² flasks. Cell culture medium used was RPMI 1640 (GIBCO, Grand Island, N.Y.) supplemented with 100 ng/ml penicillin, 100 U/ml streptomycin (Glaxo, Boronia, Victoria, Australia), 2 mM L-glutamine, $5 \times 10^{-5}$ M 2-mercaptoethanol (Sigma Chemicals, St. Louis, Mo.), and 20%

Lewis rat serum. 20% Lewis rat serum produced low background stimulation. Autologous or same species serum results in very low background stimulation. This low background is due to elimination of the response to heterologous proteins in products such as fetal calf serum that are not used in the media.

D. Activation of Naïve CD4$^+$CD25$^+$ and Emergence of CD8$^+$ T Cells

CD4$^+$CD25$^+$ T cells (8×10$^6$) from naïve DA rats (containing less than 1% CD4$^+$CD25$^-$ and less than 2% CD8 T cells) were incubated in mixed lymphocyte culture with stimulator cells (1×10$^6$) from PVG rats in the presence of 10 µg/ml IL-2 or IL-4. Proliferation of the phenotype of the cell populations after 3-6 days co-culture was determined. The results are shown in FIG. 1.

AS can be seen from FIG. 1, culturing of naïve CD4$^+$CD25$^+$ T cells in the presence of alloantigen and IL-2 or IL-4 resulted in proliferation of CD4$^+$CD25$^+$ T cells, the proliferation being maximum at day 4 for cell cultured with IL-4, and day 5 for cells cultured with IL-2.

E. FACS Analysis of Activated CD4$^+$CD25$^+$ T Cells

The CD4, CD25 and CD8 expression profile of CD4$^+$CD25$^+$ T cells from DA rats activated by culturing in the presence of stimulator cells from PVG rats and IL-2 or IL-4, unfractionated CD4$^+$ T cells and CD4$^+$CD25$^+$ T cells from naïve DA rats was determined using FACS analysis. Cells were stained with the following labelled anti-rat mAbs MRCOx35 (CD4), MRCOx8 (CD8) and MRCOx39 (CD25) (BD Biosciences Pharmingen, San Diego, Calif.). Intracellular staining of Foxp3 was performed using the FITC anti-mouse/rat Foxp3 staining set (eBioscience, San Diego, Calif.) according to the manufacturer's instructions. Immunoflourescence staining was performed as described in Nicolls M R, Aversa G G, Pearce N W, Spinelli A, Berger M F, Gurley K E, et al. Induction of long-term specific tolerance to allografts in rats by therapy with an anti-CD3-like monoclonal antibody. Transplantation 1993; 55(3):459-68).

Figure 2:
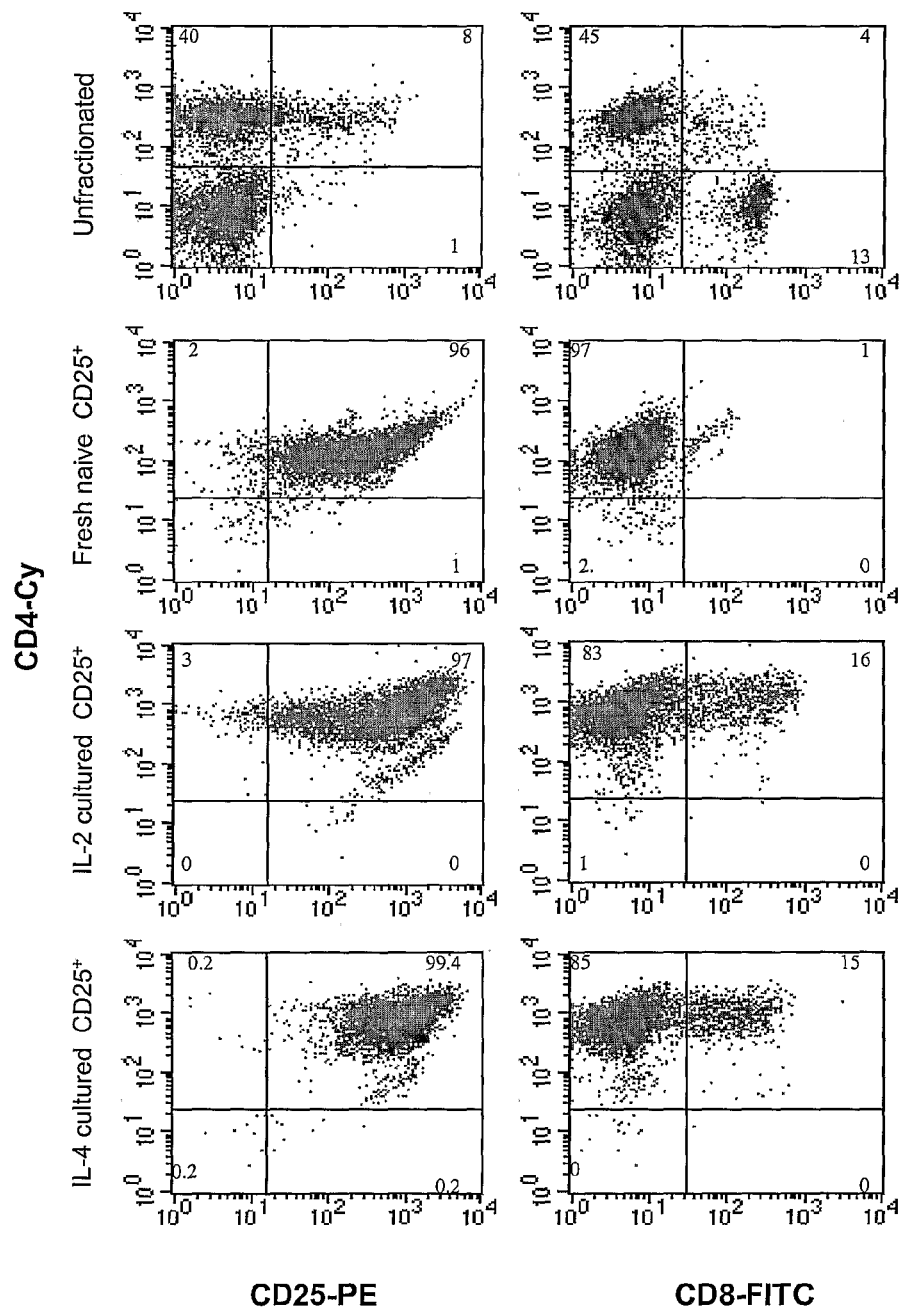
FIG. 2 shows a Fluorescent Activated Cell Sorting (FACS) analysis of peripheral lymphocyte populations isolated from naïve DA rats. Staining for CD4 (CD4-Cy) is shown on the Y axis for each panel. Staining for CD25 (CD25-PE) is shown on the X axis in the left hand column of panels. Staining for CD8 is shown on the X axis in the right hand column of panels. The top row of panels corresponds to analysis of unfractionated T cell populations. The second row of panels from the top corresponds to analysis of freshly isolated naïve $CD4^+CD25+$ T cells (fresh naïve $CD4^+CD25^+$). The third row of panels from the top corresponds to analysis of $CD4^+CD25^+$ T cells following 3 day culture of naïve $CD4^+CD25^+$ T cells with alloantigen and IL-2 (IL-2 cultured $CD25^+$). The fourth row of panels from the top corresponds to $CD4^+CD25^+$ T cells following 3 day culture of naïve $CD4^+CD25^+$ T cells with alloantigen and IL-4 (IL-4 cultured $CD25^+$).
Figure 3:
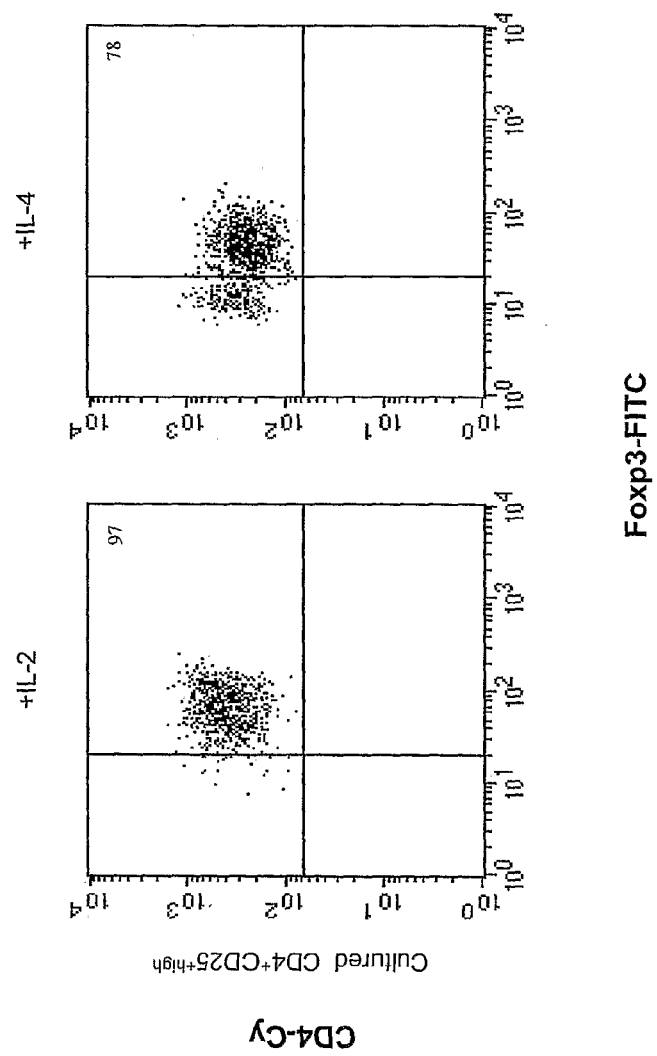
FIG. 3 shows a FACS analysis of $CD4^+CD25^+$ T cells from DA rats following 3 day culture of the $CD4^+CD25^+$ T cells with PVG alloantigen and IL-2 or PVG alloantigen and IL-4 (as indicated). Staining for Foxp3+ is shown on the X-axis.

The results of the FACS analysis is shown in FIGS. 2 and 3.

FACS analysis of unfractionated CD4+ T cells indicated that CD4$^+$CD25$^+$ T cells represent 8% of the total cells and CD4$^+$CD8$^+$ cells represent 4% of the total cell.

After depletion of CD25$^-$, CD8$^{30}$ and B cells from a CD4$^+$ population, the CD4$^+$ population was enriched for CD4$^+$CD25$^+$ cells. FACS analysis indicated that the resulting naïve CD4$^+$CD25$^+$ T cell population comprises 96% CD25$^+$ and 1% CD8$^+$, most of the latter being an artefact staining (FIG. 2, second row of panels from top).

The FACS profile of naïve CD4$^+$CD25$^+$ T cells cultured with PVG alloantigen and IL-2 showed 97% are CD25$^+$, 97% Foxp3$^+$ and 16% CD8$^+$ (FIG. 2, third row of panels from top, and FIG. 3, left hand panel). The FACS profiles of naïve CD4+CD25+ T cells cultured with PVG alloantigen and IL-4 showed that >99% were CD4$^+$, 78% Foxp3$^+$ and 15% CD8$^+$ cells (FIG. 2, fourth row from top, and FIG. 3, right hand panel).

These populations studies indicate that following activation of CD4$^+$CD25$^+$ T cells with antigen and IL-2 or IL-4, there is an emergence of a CD4$^+$CD8$^+$CD25$^+$ T cell population.

In addition, the CD25$^+$ enriched populations were stained with the following anti-rat mAbs R7.2 (TCR-α,β) and G4.18 (CD3) (BD Biosciences Pharmingen, San Diego, Calif.) as described in Transplantation 1993; 55(3):459-68. These results indicated that the CD4$^+$CD25$^+$ T cells expressed TCR-α,β and CD3, confirming that the CD4$^+$CD25$^+$ cells were T cells.

F. Inhibition of CD4$^+$CD25$^-$ Proliferation

CD4$^+$CD25$^+$ T cells from naïve DA rats were grown in bulk mixed lymphocyte culture (5-8×10$^6$ cells) with allogeneic PVG stimulator cells (1×10$^4$) as described above in cultures supplemented with IL-2.

After 3-4 days in culture, the cells all continued to express CD4 and CD25, and 10% to 30% of cells co-expressed CD8.

Three populations of CD4$^+$CD25$^+$ T cells were prepared. A prepanned population was prepared which comprised the cultured CD4$^+$CD25$^+$ T cells without further treatment (prepanned in FIGS. 4 and 5). A CD4$^+$CD8$^-$CD25$^+$ T cell population (CD8$^-$ in FIGS. 4 and 5) was prepared by depleting CD8$^+$ T cells from the cultured CD4$^+$CD25$^+$ T cells using anti-CD8 mAB (Miltenyi Biotec, Germany). A CD4$^+$CD8$^+$CD25$^+$ T cells population (CD8$^+$ in FIGS. 4 and 5) was prepared by positively selecting CD8$^+$ T cells by incubating cultured CD4$^+$CD25$^+$ T cells with an anti-CD8 mAB (Miltenyi Biotec, Germany) and harvesting the CD8$^+$ T cells.

The ability of the CD4$^+$CD25$^+$ T cell populations to suppress proliferation of fresh CD4$^+$CD25$^-$ T cells in a secondary mixed lymphocyte culture with either PVG stimulator cells or Lewis stimulator cells was investigated. The ratio of cultured CD4$^+$CD25$^+$ T cell populations (pre-panned, CD8$^-$ or CD8$^+$) to CD4$^+$CD25$^-$ T cells (1×10$^5$) was varied by serial dilution of the CD4$^+$CD25$^+$ T cell populations from 1:1. The 1:1 ratio contained 1×10$^5$ CD4$^+$CD25$^+$ T cells and 1×10$^5$ CD4$^+$CD25$^-$ T cells. All incubations were in the presence of either PVG or Lewis (as indicated) stimulator cells (1×10$^4$ stimulator cells) in U-bottom microtiter plates (Linbro, Flow Labs, Va.) in a total volume of 200 µl. 4-6 replicate wells were set up for each experimental sample.

Cells were cultured at 37° C. in humidified air containing 5% CO$_2$ and at various time points, usually at 3, 4, 5 and 6 days the cultures were pulsed with 0.5 µCi $^3$H-TdR (Amersham, Arlington Heights, Ill.) 16 hr prior to harvesting with a Titretek Cell Harvester (Flow Lab, Ayrshire, Scotland). Proliferation was assayed by adding liquid scintillation fluid before counting on a beta counter (1450 Microbeta Plus, Beckman Instruments, Palo Alto, Calif.).

Figure 4:
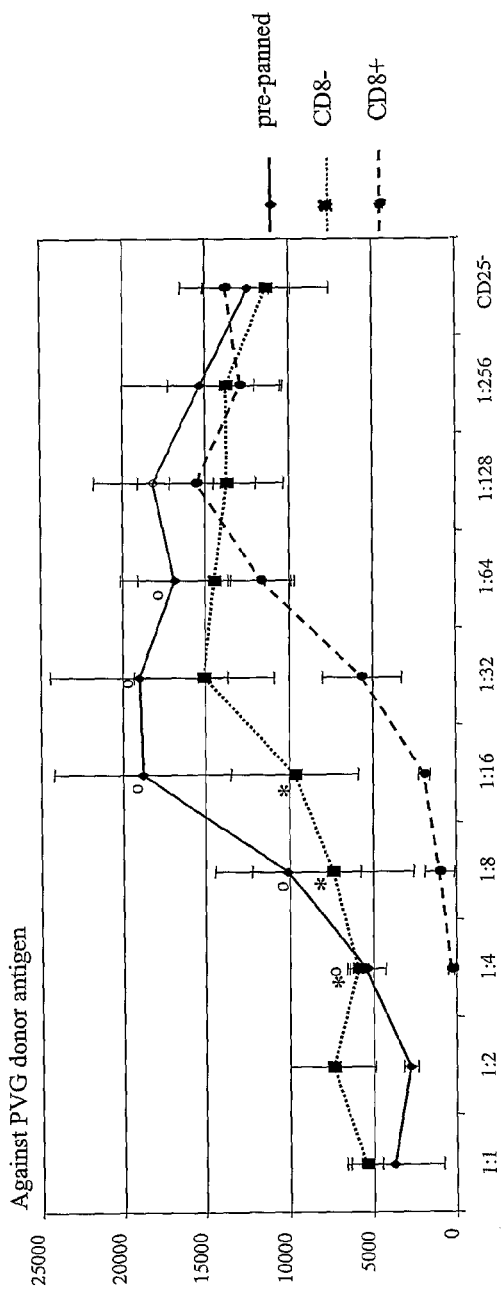
FIG. 4 is a graph of the proliferation in response to PVG antigen of $CD4^+CD25^-$ T cells (on y axis) following incubation of the $CD4^+CD25^-$ T cells with serial dilutions (shown on x axis) of populations of $CD4^+CD25^+$ T cells which have been activated to PVG antigen. The populations of $CD4^+CD25^+$ T cells are as follows: unfractionated population containing both $CD8^+CD4^+CD25^+$ T cells and $CD8^-CD4^+$ $CD25^+$ T cells (pre-panned), population depleted of $CD8^+$ $CD4^+CD25^+$ T cells ($CD8^-$), and population of enriched $CD8^+CD4^+CD25^+$ T cells ($CD8^+$).
Figure 5:
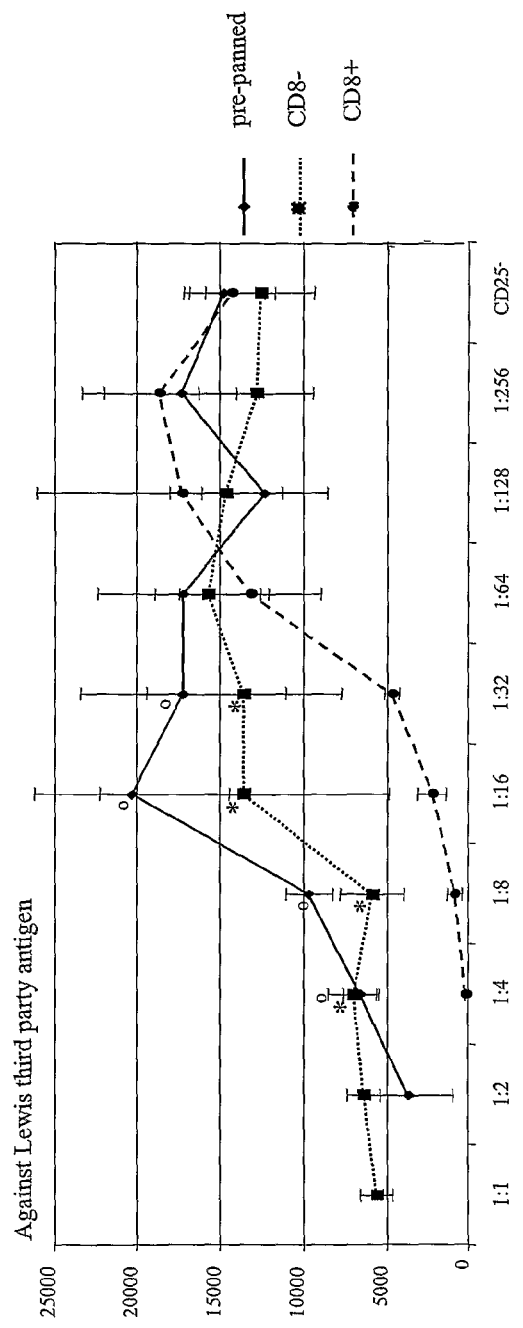
FIG. 5 is a graph of the proliferation in response to Lewis alloantigen of $CD4^+CD25^-$ T cells (on y axis) following incubation of the $CD4^+CD25^-$ T cells with serial dilutions (shown on x axis) of populations of $CD4^+CD25^+$ T cells activated to PVG antigen. The populations of $CD4^+CD25^+$ T cells are as follows: unfractionated population containing both $CD8^+CD4^+CD25^+$ T cells and $CD8^-$ $CD4^+CD25^+$ T cells (pre-panned), population depleted of $CD8^+CD4^+CD25^+$ T cells ($CD8^-$), and population enriched $CD8^+CD4^+CD25^+$ T cells ($CD8^4$).

FIGS. 4 and 5 show that full suppression of CD4$^+$CD25$^-$ T cell proliferation in response to PVG or Lewis antigen was obtained with 1:4 dilution of isolated CD4$^+$CD8$^+$CD25$^+$ T cells and significant suppression with this subset was achieved out to a 1:64 dilution. The same level of suppression by unfractionated (pre-panned) or CD8-depleted populations was only observed at 1:1, 1:2, 1:4 and 1:8 dilutions. However, unfractionated and CD8 depleted populations never fully suppressed CD4$^+$CD25$^-$ T cell proliferation in response to PVG or Lewis antigen.

In both FIGS. 4 and 5, * indicates p<0.05 which indicates a statistically significant difference in the ability of CD4$^+$CD8$^+$CD25$^+$ T cells and CD4$^+$CD8$^-$CD25$^+$ T cells to suppress CD4$^+$CD25$^-$ T cell proliferation. ° indicates p<0.05 which indicates a statistically significant difference in ability of CD4$^+$CD8$^+$CD25$^+$ T cells and unfractionated CD4$^+$CD25$^+$ T cells to suppress CD4$^+$CD25$^-$ T cell proliferation.

These studies indicate that the greatest suppression of CD4$^+$CD25$^-$ T cell proliferation is obtained with a population of CD4$^+$CD8$^+$CD25$^+$ T cells which emerge following activation of naïve CD4$^+$CD25$^+$ T cells.

G. Activated CD4+CD25+ T Cells Induce Tolerance to Heart Allografts

The capacity of IL-2 activated CD4+CD25+ T cells to suppress rejection was examined in an adoptive transfer assay. The adoptive transfer assay was conducted as described previously (see J. Exp. Med. 1990 171(1): 141-157; J. Exp. Med. 1978, 148: 878-889 and Transplantation 1993, 55: 374-379). Briefly, DA rats were subjected to 7Gy whole body irradiation in a linear accelerator and grafted with either a PVG or Lewis heterotopic heart allograft that had also been irradiated with 700-800 rads from a Siemens Mevatron Linear accelerator irradiator 6MV). In this model, rejection is ablated unless hosts are restored with naïve CD4+ T cells, which restores rejection to 10-20 days as described (J. Exp. Med. 1990 171(1): 141-157; J. Exp. Med. 1978, 148: 878-889; Transplantation 1993, 55: 374-379; J. Immunol. 1998 161(10): 5147-5156). To test the suppressive effects of CD4+CD25+ T cells, these were co-administered with naïve CD4+ T cells.

Irradiated hosts were divided into 4 groups allocated groups A, B, C and D. In group A, 12 rats were each administered $5 \times 10^6$ naïve CD4+ T cells. In group B, 9 rats were each administered $5 \times 10^6$ naïve CD4+ T cells and $5 \times 10^5$ naïve CD4+CD25+ T cells. In group C, 6 rats were each administered $5 \times 10^6$ naïve CD4+ T cells and $5 \times 10^5$ CD4+CD25+ T cells activated to PVG antigen in the presence of IL-2. In group D, 3 rats were each administered $5 \times 10^6$ naïve CD4+ T cells and $5 \times 10^5$ CD4+CD25+ T cells activated to PVG antigen in the presence of IL-2 and depleted of CD8+ T cells (CD25+ CD8−).

Graft rejection was monitored by palpation of contraction, and severe rejection was defined as major swelling, much reduced contraction and slowing of heart rate, equivalent to graft function that would be unable to sustain life if it were a functioning heart.

Figure 6:
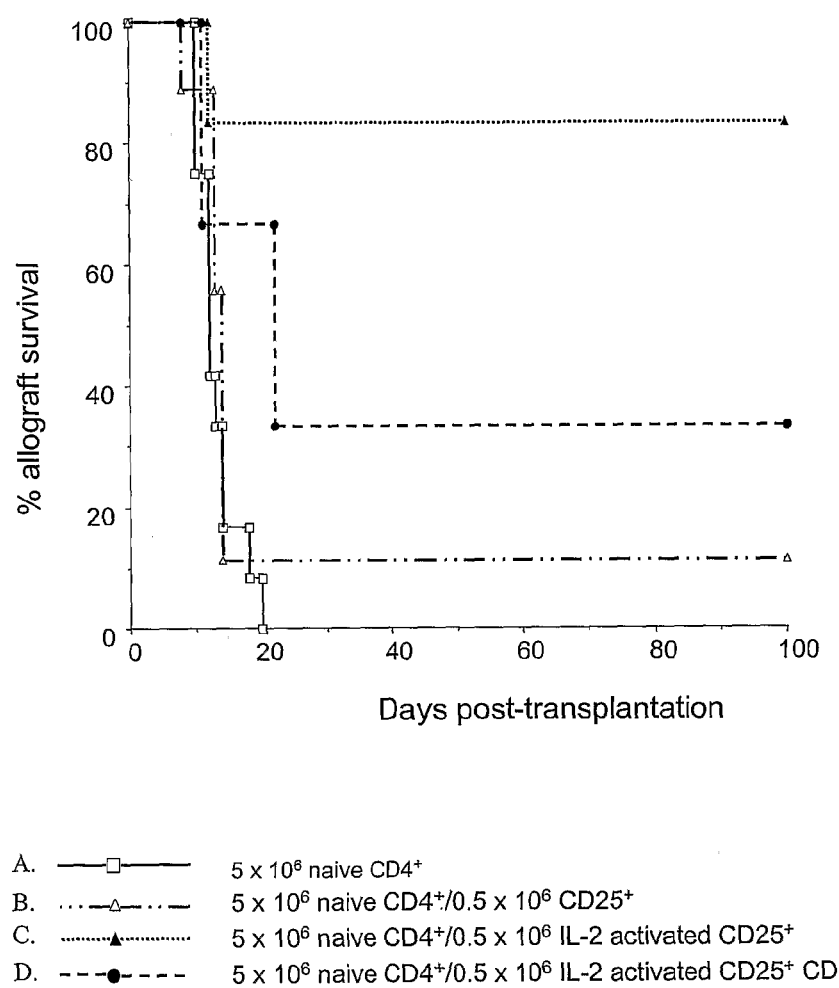
FIG. 6 is a graph showing survival of PVG heart grafts in irradiated DA rats following administration of: A. a population of $5 \times 10^6$ naïve $CD4^+$ T cells (solid line, open squares); B. a mixture of $5 \times 10^6$ naïve $CD4^+$ T cells and $5 \times 10^5$ isolated $CD4^+CD25^+$ T cells (broken line with dots, open triangles); C. a mixture of $5 \times 10^6$ naïve $CD4^+$ T cells and $5 \times 10^5$ $CD4^+$ $CD25^+$ T cells which had been cultured for 3 days with PVG antigen in the presence of IL-2 (dotted line, closed triangles); and D. a mixture of $5 \times 10^6$ naïve $CD4^+$ T cells and $5 \times 10^5$ $CD4^+CD25^+$ T cells which had been cultured for 3 days with PVG antigen in the presence of IL-2 from which $CD8^+$ cells have subsequently been depleted (dashed line, closed triangles).

The results are shown in FIG. 6.

The percent of grafts surviving long term were as follows:
Group A 0%
Group B 11%
Group C 84%
Group D 33%.

Irradiated hosts treated with $5 \times 10^6$ CD4+ T cells showed rejection of the transplant occurring 11-20 days post-transplantation indicating that the hosts immune response was restored with $5 \times 10^6$ CD4+ T cells.

Co-transfer of fresh naïve CD4+CD25+ T cells ($5 \times 10^5$) with $5 \times 10^6$ CD4+ T cells at a physiological ratio of 1:10 did not suppress rejection by the CD4+ T cells ($5 \times 10^6$) (see B in FIG. 6).

However, after CD4+CD25+ T cells from DA rats are cultured with PVG stimulator cells and either IL-2 or IL-4, they could suppress rejection of PVG but not third party Lewis grafts at a ratio of 1:10 with naïve CD4+ T cells (see C in FIG. 6). This demonstrated that culture with PVG stimulators and either IL-2 or IL-4 enhanced the capacity of the CD4+CD25+ T cells to suppress in an alloantigen specific manner.

The role of CD4+CD8+CD25+ in the antigen specific suppression was investigated by depleting CD8+ T cells from CD4+CD25+ T cells activated to the PVG antigen. Depletion of the CD8+ cells removed the capacity of these activated CD4+CD25+ T cells to suppress PVG rejection. This indicated that the enhanced capacity of IL-2 activated CD4+CD25+ T cells to suppress after culture with IL-2 and alloantigen was due to the subpopulation which acquired expression of CD8, indicating CD8 is a marker of antigen specific T regulatory cells.

The invention claimed is:

1. A method of preparing a population of activated CD4+CD25+CD8+ T cells comprising:
   (a) providing a population of isolated CD4+CD25+ T cells;
   (b) contacting the population of isolated CD4+CD25+ T cells with an alloantigenic antigen presenting cell, in the presence of a factor selected from the group consisting of IL-2 and IL-4, for a sufficient time to permit proliferation of the CD4+,CD25+ T cells; and
   (c) isolating CD4+CD25+CD8+ T cells from the proliferated CD4+CD25+ T cells.

2. The method of claim 1, comprising the further step, after step (c), of (d) growing the CD4+CD25+CD8+ T cells in the presence of at least one factor selected from the group consisting of IL-2, IL-4, IL-5, IL-12, IL-23, IL-10, IFN-gamma, TGF-beta, and a nitric oxide inhibitor.

3. The method of claim 2, wherein the factor is IL-2.

4. The method of claim 2, wherein the factor is IL-4.

5. The method of claim 2, wherein the factor is IL-5.

6. The method of claim 2, wherein the factor is IL-12.

7. The method of claim 2, wherein the factor is IFN-gamma.

8. The method of claim 2, wherein the factor is IL-10.

9. The method of claim 2, wherein the factor is IL-23.

10. The method of claim 2, wherein the factor is TGF-beta.

11. The method of claim 2, wherein the factor is a nitric oxide inhibitor.

* * * * *